United States Patent
Aber et al.

(10) Patent No.: US 10,905,807 B2
(45) Date of Patent: Feb. 2, 2021

(54) HIGH EFFICIENCY BLOOD PUMP

(71) Applicant: EVERHEART SYSTEMS INC., Webster, TX (US)

(72) Inventors: Greg S. Aber, Houston, TX (US); Edward D. Grainger, Pearland, TX (US)

(73) Assignee: CORVION, INC., Webster, TX (US)

( * ) Notice: Subject to any disclaimer, the term of this patent is extended or adjusted under 35 U.S.C. 154(b) by 197 days.

(21) Appl. No.: 16/035,512

(22) Filed: Jul. 13, 2018

(65) Prior Publication Data

US 2019/0015569 A1   Jan. 17, 2019

Related U.S. Application Data

(60) Provisional application No. 62/571,708, filed on Oct. 12, 2017, provisional application No. 62/532,212, filed on Jul. 13, 2017.

(51) Int. Cl.
*A61M 1/10* (2006.01)
*A61M 1/12* (2006.01)

(52) U.S. Cl.
CPC ........ *A61M 1/1015* (2014.02); *A61M 1/1017* (2014.02); *A61M 1/1036* (2014.02); *A61M 1/122* (2014.02); *A61M 1/1031* (2014.02); *A61M 2205/8206* (2013.01); *A61M 2207/10* (2013.01)

(58) Field of Classification Search
CPC .............. A61M 1/1015; A61M 1/1036; A61M 1/1017; A61M 1/22
USPC ......................................................... 600/16
See application file for complete search history.

(56) References Cited

U.S. PATENT DOCUMENTS

| | | |
|---|---|---|
| 5,049,134 A | 9/1991 | Golding et al. |
| 5,370,509 A | 12/1994 | Golding et al. |
| 5,695,471 A | 12/1997 | Wampler |
| 5,840,070 A | 11/1998 | Wampler |
| 5,890,883 A | 4/1999 | Golding et al. |
| 5,947,703 A | 9/1999 | Nojiri et al. |

(Continued)

FOREIGN PATENT DOCUMENTS

| | | |
|---|---|---|
| EP | 2554191 | 2/2013 |
| WO | WO 86/00672 | 1/1986 |

OTHER PUBLICATIONS

International Search Report and Written Opinion from PCT/US2018/042144, dated Oct. 16, 2018, 15 pages.

*Primary Examiner* — Amanda K Hulbert
*Assistant Examiner* — Philip C Edwards
(74) *Attorney, Agent, or Firm* — Nathan S. Smith; Mark I. Bentley; Morgan, Lewis & Bockius LLP

(57) ABSTRACT

Blood pumps discussed herein may be suitable for use as a ventricular assist device (VAD) or the like. The blood pumps cause minimal blood damage, are energy efficient, and can be powered by implanted batteries for extended periods of time. Further, these pumps are also beneficial because they may improve the quality of life of a patient with a VAD by reducing restrictions on the patient's lifestyle. The blood pumps can provide radial and axial stability to a rotating impeller that is driven by a separate rotor. Both radial and axial stability can be provided, at least in part, by one or more permanent magnetic couplings between the rotor and the impeller and/or one or more permanent magnetic bearings between the pump housing and the impeller.

21 Claims, 15 Drawing Sheets

(56) References Cited

U.S. PATENT DOCUMENTS

| | | |
|---|---|---|
| 6,015,272 A | 1/2000 | Antaki et al. |
| 6,080,133 A | 6/2000 | Wampler |
| 6,688,861 B2 | 2/2004 | Wampler |
| 7,189,260 B2 | 3/2007 | Horvath et al. |
| 7,575,423 B2 | 8/2009 | Wampler |
| 7,997,854 B2 | 8/2011 | Larose et al. |
| 8,512,013 B2 | 8/2013 | Larose et al. |
| 8,540,477 B2 | 9/2013 | Larose et al. |
| 8,932,006 B2 | 1/2015 | Larose et al. |
| 9,242,032 B2 | 1/2016 | Larose et al. |
| 2003/0124007 A1 | 7/2003 | Schima et al. |
| 2005/0025630 A1 | 2/2005 | Ayre et al. |
| 2005/0095151 A1 | 5/2005 | Wampler et al. |
| 2011/0238172 A1 | 9/2011 | Akdis |
| 2012/0089225 A1* | 4/2012 | Akkerman .......... A61M 1/1017 623/3.13 |
| 2014/0046118 A1* | 2/2014 | LaRose .............. A61M 1/1029 600/16 |
| 2014/0255225 A1* | 9/2014 | Aber ................. A61M 1/1036 417/420 |
| 2015/0118021 A1* | 4/2015 | LaRose .............. A61M 1/1017 415/106 |
| 2016/0138597 A1* | 5/2016 | LaRose .............. A61M 1/1029 417/420 |

\* cited by examiner

SECTION A-A

SECTION B-B

DETAIL C

SECTION A-A

SECTION B-B

DETAIL C

DETAIL D

HIGH EFFICIENCY BLOOD PUMP

CROSS-REFERENCE TO RELATED APPLICATIONS

This application claims the benefit of U.S. Provisional Application No. 62/532,212, entitled "HIGH EFFICIENCY BLOOD PUMP," filed Jul. 13, 2017, and U.S. Provisional Application No. 62/571,708, entitled "HIGH EFFICIENCY BLOOD PUMP," filed Oct. 12, 2017, the entirety of each of which is incorporated herein by reference.

TECHNICAL FIELD

The present description relates in general to blood pumps, and more particularly to, for example, without limitation, implantable rotary blood pumps.

BACKGROUND OF THE DISCLOSURE

Implantable blood pumps can be utilized for total artificial heart replacement or ventricular assistance. Implantable blood pumps may be utilized for temporary or long term ventricular assistance or to permanently replace a patient's damaged heart.

Figure 1:
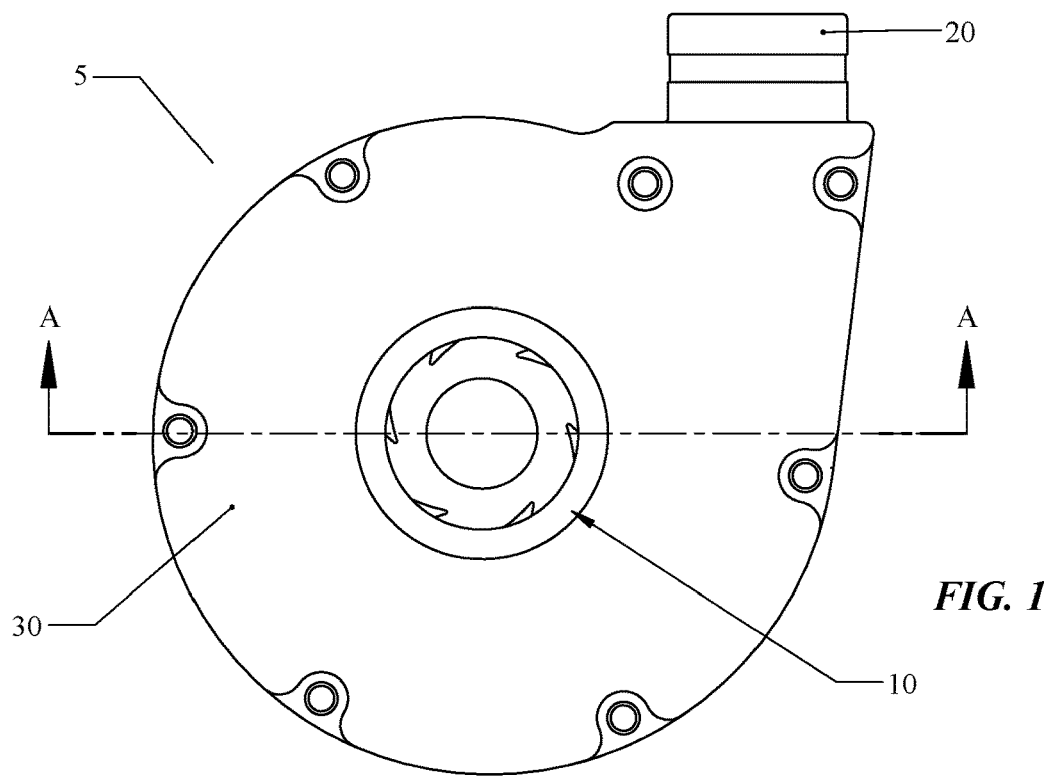
FIG. 1 shows a top plan view of an illustrative embodiment of a pump.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

Referring to the drawings, depicted elements are not necessarily shown to scale, and like or similar elements are designated by the same reference numeral through several views. In some embodiments, the depicted elements can be provided with the relative size and positions shown in the several views. Additionally or alternatively, the depicted elements can be provided with relative sizes and positions other than those shown in the several views.

Implantable blood pumps can be utilized for total artificial heart replacement or ventricular assistance. Implantable blood pumps may be utilized for temporary or long term ventricular assistance or to permanently replace a patient's damaged heart. Some blood pumps may mimic the pulsatile flow of the heart. However, some blood pumps have progressed to designs that are non-pulsatile. Non-pulsatile blood pumps are typically rotary and propel fluid with impellers that span the spectrum from radial flow, centrifugal type impellers to axial flow, auger type impellers.

A common issue encountered by blood pumps is blood trauma. The causes of blood trauma can be partially attributed to shear stress and/or heat generated by the bearings supporting the impeller. Shear stress and/or heat may cause hemolysis, thrombosis, and the like. In some blood pumps, the impeller may be driven by a shaft. The shaft may be sealed off with shaft seals to prevent blood from entering undesirable areas, such as a motor driving the shaft. However, shaft seals generate excess heat that may produce blood clots, and shaft seals may fail and allow blood to enter unwanted areas.

A great deal of effort has been devoted to reducing or eliminating blood trauma in rotary blood pumps. One solution to minimizing or eliminating blood trauma is to provide hydrodynamic support of the impeller.

For example, hydrodynamic support may be provided by ramp, wedge, plain journal, multi-lobe or groove hydrodynamic bearings. Another solution is to provide mechanical support of the impeller using mechanical bearings, such as jewel type bearings in the form of a shaft and sleeve or ball and cup. These mechanical bearings may utilize biocompatible hard ceramic materials. To function properly in blood, a mechanical bearing must generate very little heat and should avoid stagnant or recirculating areas of blood flow to prevent the formation of blood clots. Another solution proposed is the utilization of passive permanent magnetic and active controlled magnetic bearings to provide impeller support in blood pumps. Magnetic bearings, hydrodynamic bearings, and/or mechanical bearings may be combined to provide impeller support in blood pumps.

However, in accordance with at least some of the embodiments disclosed herein is the realization that active magnetic bearing systems may require sensors and complex controls that increase cost and decrease reliability. Hydrodynamic bearings may require small clearances which may cause slow moving or stagnant blood flow between hydrodynamic bearing surfaces. Further, some blood pumps incorporate electric motors into the pumping chamber, rather than providing separate motor and pumping chambers. For example, a stator may be provided in the pump housing and magnets can be incorporated into an impeller to provide a pump impeller that also functions as the rotor of the electric motor.

Heart pumps that are suitable for adults may call for approximately 5 liters/min of blood flow at 100 mm of Hg pressure, which equates to about 1 watt of hydraulic power. Some implantable continuous flow blood pumps consume significantly more electric power to produce the desired amount of flow and pressure.

High power consumption makes it impractical to implant a power source in the body. For example, size restrictions of implantable power sources may only allow the implantable power source to provide a few hours of operation. Instead, high power consumption blood pumps may provide a wire connected to the pump that exits the body (i.e., percutaneous) for connection to a power supply that is significantly larger than an implantable power source. These blood pumps may require external power to be provided at all times to operate. In order to provide some mobility, external bulky batteries may be utilized. However, percutaneous wires and external batteries can still restrict the mobility of a person with such a blood pump implant. For example, such high power consumption blood pumps have batteries that frequently require recharging thereby limiting the amount of time the person can be away from a charger or power source, batteries that can be heavy or burdensome thereby restricting mobility, percutaneous wires that can lead to infection and are not suitable for prolonged exposure to water submersion (e.g., swimming, bathing, etc.), and/or other additional drawbacks.

The various embodiments of blood pumps discussed herein may be suitable for use as a ventricular assist device (VAD) or the like because they cause minimal blood damage, are energy efficient, and can be powered by implanted batteries for extended periods of time. Further, these pumps are also beneficial because they may improve the quality of life of a patient with a VAD by reducing restrictions on the patient's lifestyle.

The various embodiments of blood pumps discussed herein can provide radial, axial, and angular stability to a rotating impeller that is driven by a separate rotor. Both radial and axial stability can be provided, at least in part, by one or more permanent magnetic couplings between the rotor and the impeller and/or permanent magnetic bearings between the pump housing and the impeller. For example, adequate radial stability can be provided solely by the magnetic coupling. By further example, axial stability can be provided by balanced forces from the magnetic coupling, a hydrodynamic bearing, and/or fluid pressure and flow about the impeller. Angular stability, defined as the impeller rotating about an axis that is aligned and coaxial with its principle geometric axis, can be improved by gyroscopic forces created by the rotational inertia of the impeller itself. Adequate stability can achieve suspension of the impeller without contacting any portion of the housing. For example, the impeller can rotate and remain in contact with only the fluid. Stability can include a balance of opposing forces, where the impeller is balanced by being held in equilibrium between the opposing forces.

Figure 2:
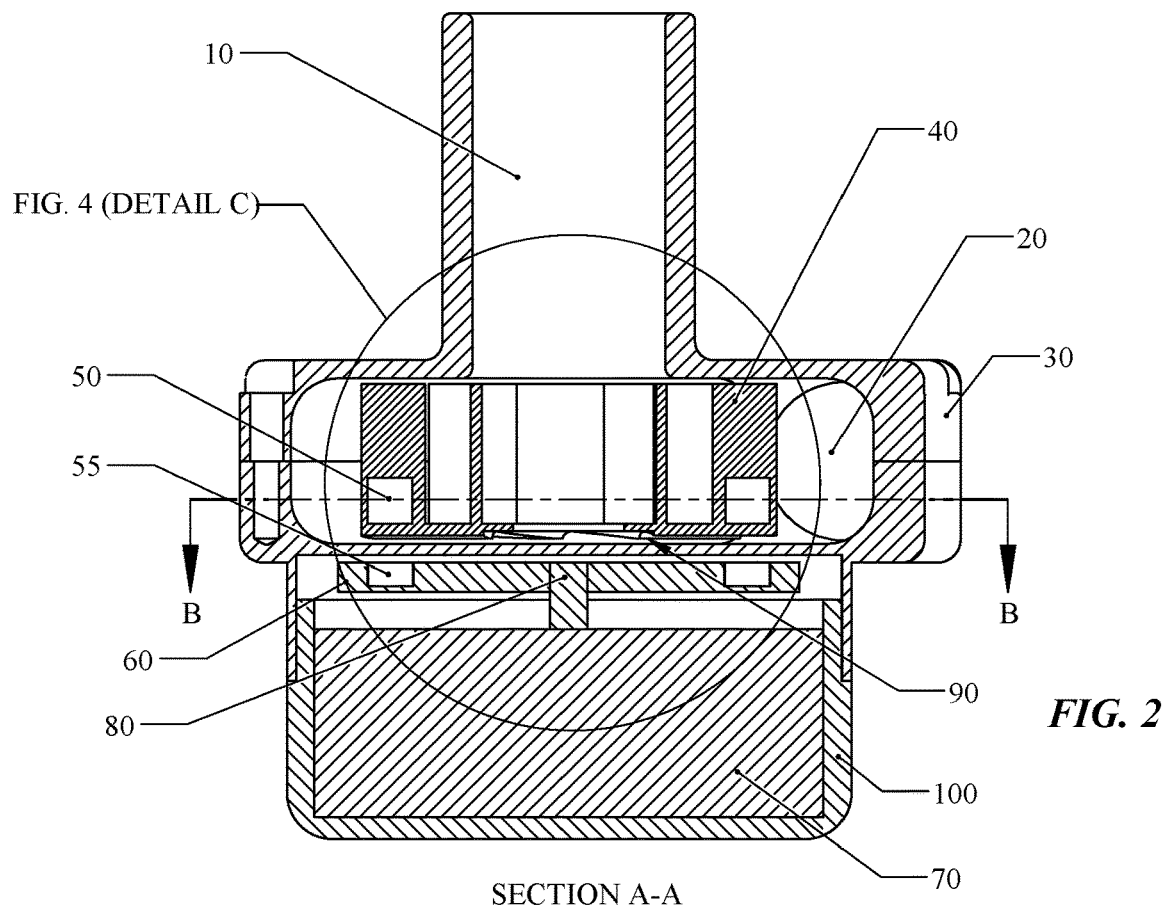
FIG. 2 shows a cross-sectional side view of the pump taken along section lines A-A of FIG. 1.
Figure 3:
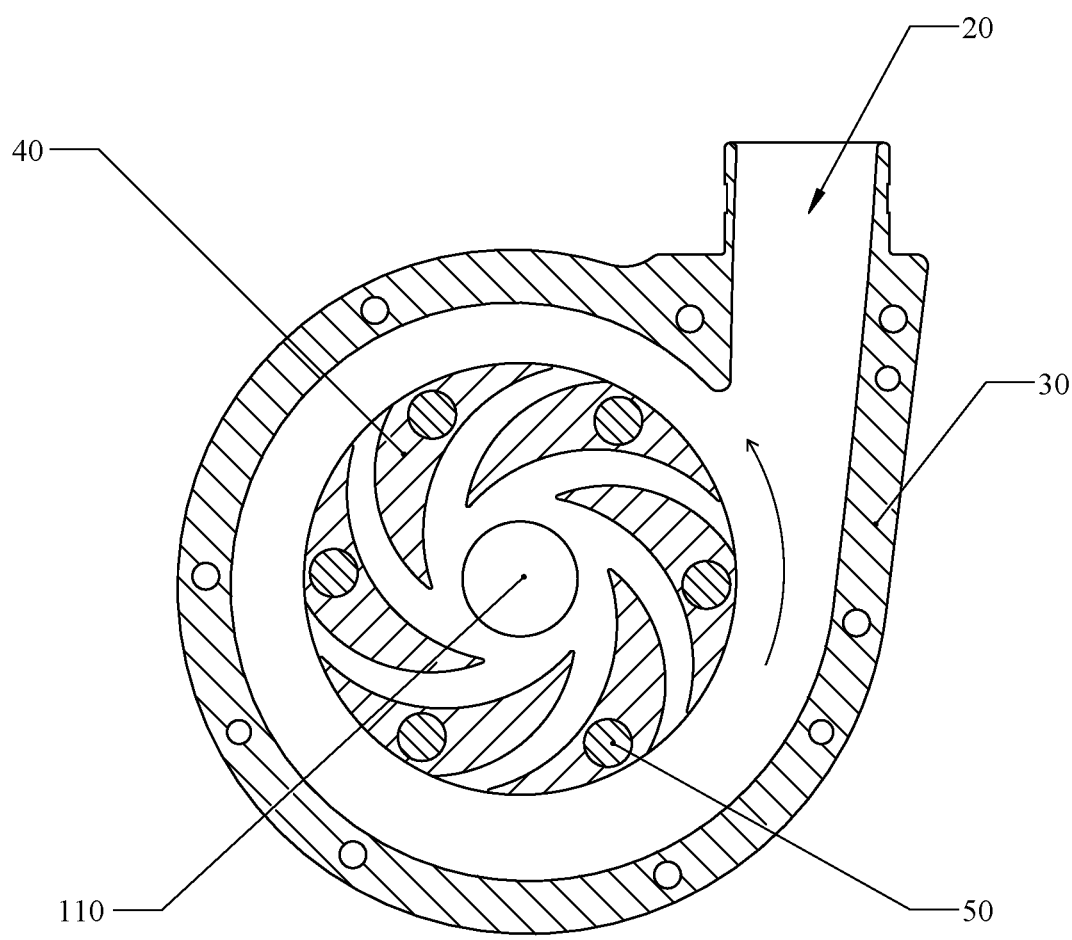
FIG. 3 shows a cross-sectional top view of the pump taken along section lines B-B of FIG. 2.

The following description provides an implantable, energy efficient, small, and magnetically driven blood pump. FIG. 1 shows a top view of an illustrative embodiment of pump 5. In some embodiments, pump 5 is formed from pump housing 30 providing inlet 10, outlet 20, and motor housing 100. Pump housing 30 is composed of two or more pieces. FIG. 2 shows a cross-sectional side view of an illustrative embodiment of pump 5. In some embodiments, pump housing 30 provides a chamber for impeller 40 to rotate within. The impeller chamber has inlet 10 for connection to a fluid source and outlet 20 for providing fluid to a desired location. The impeller chamber is sealed and pressure tight to prevent fluid from entering/exiting the impeller chamber from locations other than inlet 10 and outlet 20.

Figure 5A:
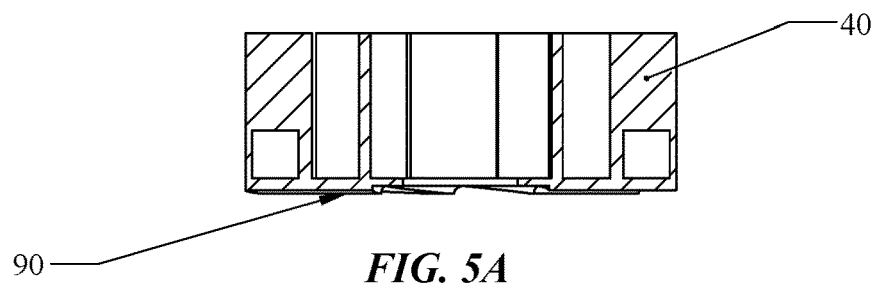
FIG. 5A shows a cross-sectional view of an impeller.
Figure 5B:
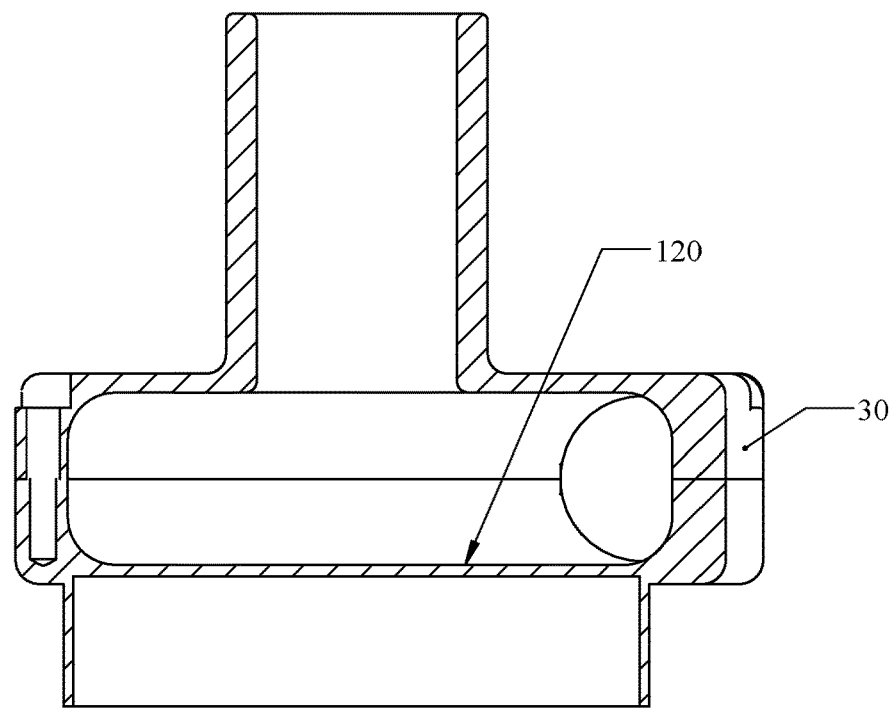
FIG. 5B shows a cross-sectional view of an illustrative embodiment of a pump housing.
Figure 5C:
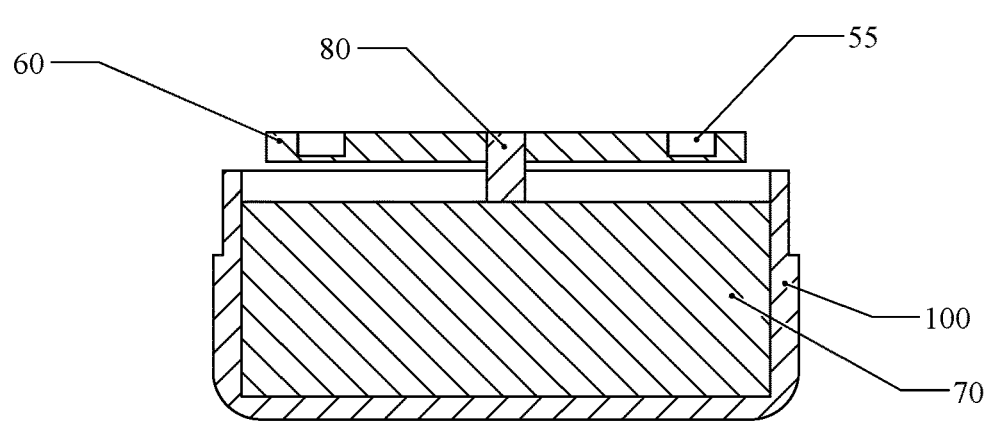
FIG. 5C shows a cross-sectional view of an illustrative embodiment of a motor and motor housing.

Motor housing 100 is attached to pump housing 30 to form a fluid and/or pressure tight chamber for motor 70. While pump housing 30 is shown as a separate component from motor housing 100, in other embodiments, pump housing 30 and motor housing 100 may be combined to form a single, combined housing, for example, formed as a single, continuous part. An exploded, cross-sectional view of an illustrative embodiment of motor 70 and motor housing 100 is also shown in FIGS. 5A-5C.

In accordance with some embodiments, motor housing 100 is shown separate from pump housing 30. Motor 70 is entirely contained between pump housing 30 and motor housing 100. A high-efficiency electric motor can be utilized, such as an electric motor with efficiency of about 85% or greater. Motor 70 provides shaft 80 with carrier 60 mounted to shaft 80. Carrier 60 contains one or more permanent magnets and/or magnetic materials. The motor 70 rotates shaft 80, causing carrier permanent magnets 55 placed in carrier 60 to rotate. The motor 70 can include a stator with one or more coils (not shown) and a rotor with one or more permanent magnets (not shown) that drive the shaft 80. Accordingly, the motor 70 can directly drive the shaft 80 and carrier 60, rather than directly driving the impeller 40.

As shown in FIGS. 4 and 6A-6C, the impeller 40 can comprise one or more arc-shaped segments or blades joined by a disc or ring at the bottom of impeller 40. Alternately, the blades may be joined by short and thin ribs, struts, or bridges connecting the blades thereby eliminating the bottom disc or ring. One or more of the blades of impeller 40 can comprise one or more permanent magnets and/or magnetic materials, which can be arranged to attract to one or more carrier permanent magnets 55 in an axial direction (i.e., along an axis of rotation of the impeller 40). Alternately, impeller permanent magnets 50 can reside partially or wholly in the bottom disc or ring joining the impeller blades. Carrier permanent magnets 55 and impeller permanent magnets 50 may form an axial magnetic coupling to transmit torque from motor 70 to impeller 40. Rotation of the carrier 60 causes impeller 40 to rotate and move fluid from inlet 10 to outlet 20.

As used herein, "magnet" can include a magnet of a hard magnetic material and/or a magnet of a soft magnetic material. Hard magnetic materials include materials that retain their magnetism even after the removal of an applied magnetic field. Magnets that include hard magnetic material can form permanent magnets. Hard magnetic materials include neodymium (NdFeB), iron-neodymium, iron-boron, cobalt-samarium, iron-chromium-cobalt, and combinations or alloys thereof. Soft magnetic materials include materials that are responsive to magnetic fields, but do not retain their magnetism after removal of an applied magnetic field. Magnets that include soft magnetic material can form temporary magnets. Soft magnetic materials include iron, iron-cobalt, iron-silicon, steel, stainless steel, iron-aluminum-silicon, nickel-iron, ferrites, and combinations or alloys thereof. It will be recognized that "hard magnetic" and "soft magnetic" does not necessarily relate to the rigidity of the materials.

Figure 4:
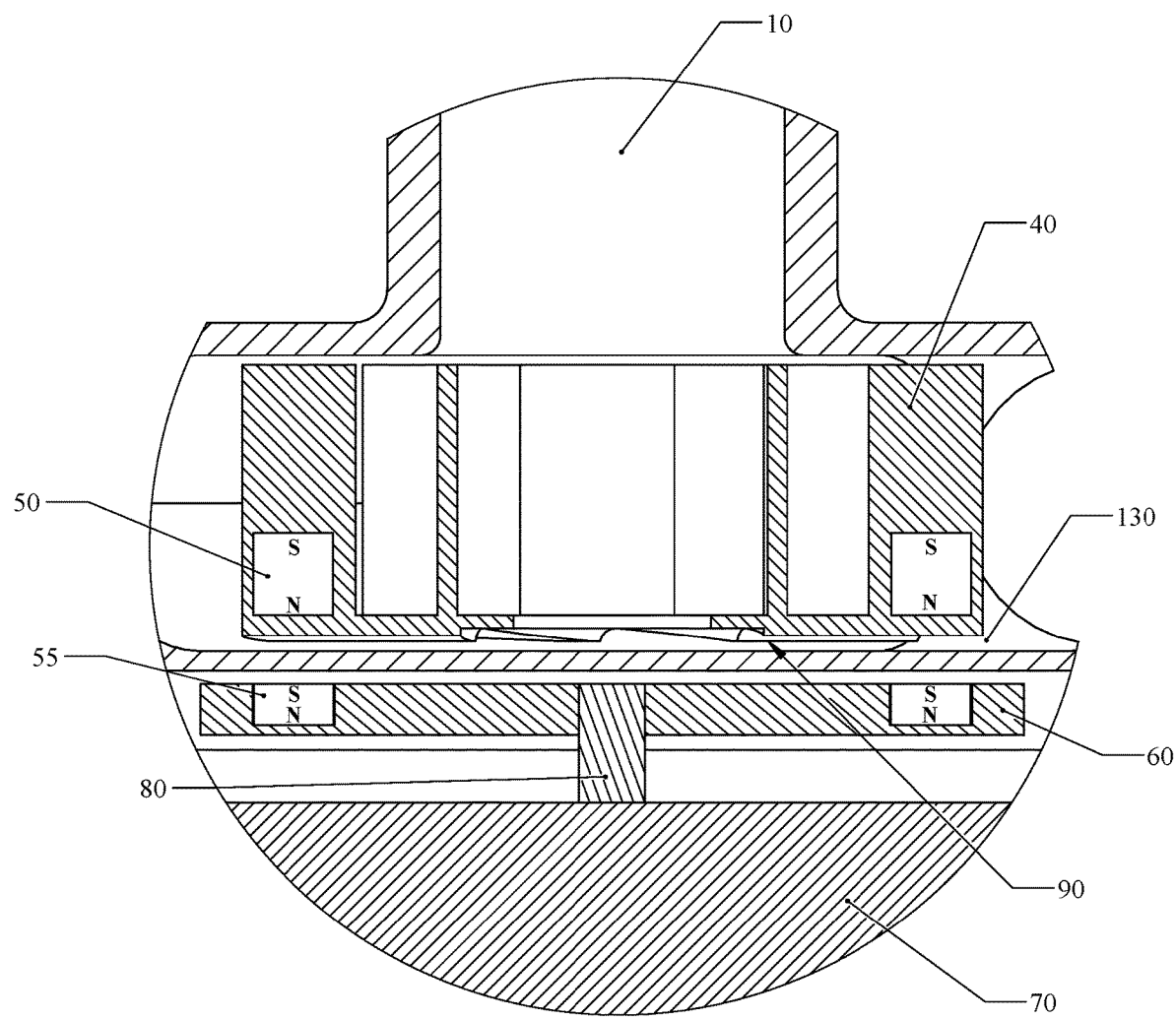
FIG. 4 shows an enlarged cross-sectional side view of the pump of section C of FIG. 2.

In accordance with some embodiments, as shown in FIG. 4, the one or more impeller permanent magnets 50 and one or more carrier permanent magnets 55 can be arranged to attract in the axial direction (e.g., along an axis of rotation of the impeller). The impeller permanent magnets 50 and carrier permanent magnets 55 can create magnetic forces that can act to restrain impeller motion in the radial direction during rotation thereby forming a radial magnetic bearing. As used herein, a magnetic bearing is one that supports an impeller in the indicated direction by tending to move the impeller to a position of equilibrium. For example, a radial magnetic bearing can balance the impeller in a radial direction. The magnets need not be aligned radially to achieve radial stability of the impeller. Indeed, various magnets disclosed herein form an axial magnetic coupling to provide radial stability with a radial magnetic bearing. By further example, an axial magnetic bearing can balance the impeller in an axial direction. The magnets need not be aligned axially to achieve axial stability of the impeller. Indeed, various magnets disclosed herein form a radial magnetic coupling to provide axial stability with an axial magnetic bearing.

The impeller permanent magnets 50 may be sufficiently small in size so that they have little or no impact on the main fluid flow paths of impeller 40 thereby allowing the design of impeller 40 to focus on fully optimizing pump efficiency. These benefits can allow pumping efficiencies of greater than 50% to be achieved.

In some embodiments, no additional mechanism is required to radially stabilize the impeller 40 during rotation. For example, in some embodiments, only the axially attracting impeller permanent magnets 50 and carrier permanent magnets 55 provide radial stability to the impeller 40. In some embodiments, no magnetic coupling or bearing is required radially across or spaced apart from or within the impeller 40. In some embodiments, no support structure is required radially across or spaced apart from or within the impeller 40, for example, to form a hydrodynamic or magnetic bearing.

As used herein, components that are radially across from each other or radially spaced apart from each other are aligned so that they have overlapping portions (e.g., as viewed from a side) while being different radial distances away from an axis. For example, the components can be overlapping by having positions that are both aligned with a common portion of the axis.

As used herein, components that are axially across from each other or axially spaced apart from each other are aligned so that they have overlapping portions (e.g., as viewed from above or below) while being a same distance away from an axis. For example, the components can be overlapping by being arranged along an axis that is parallel to an axis of impeller rotation.

Pump housing 30 provides a bearing surface 120. Impeller 40 may provide hydrodynamic bearing features 90 on its bottom surface or surfaces to form an axial hydrodynamic bearing with bearing surface 120. Hydrodynamic bearing features 90 may be ramps, wedges, steps, grooves or any other feature that creates hydrodynamic pressure during rotation.

Figure 6A:
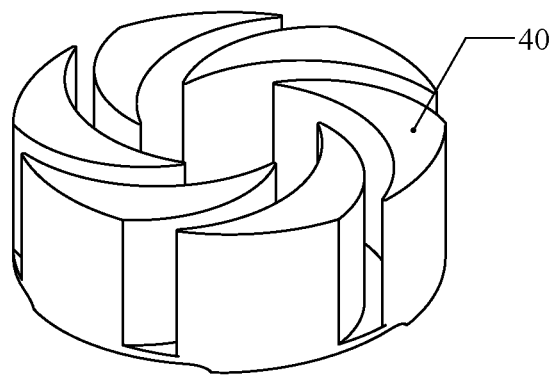
FIG. 6A shows a top perspective view of an illustrative embodiment of an impeller.
Figure 6B:
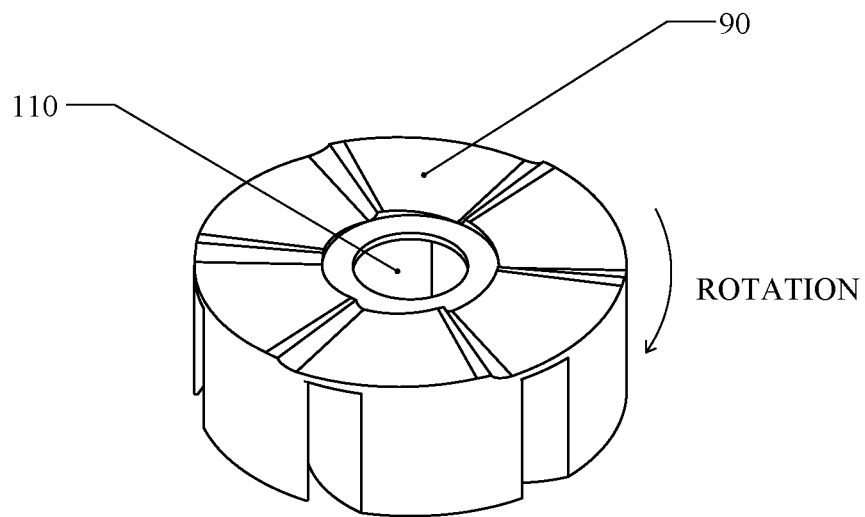
FIG. 6B shows a bottom perspective view of the impeller of FIG. 6A.
Figure 6C:
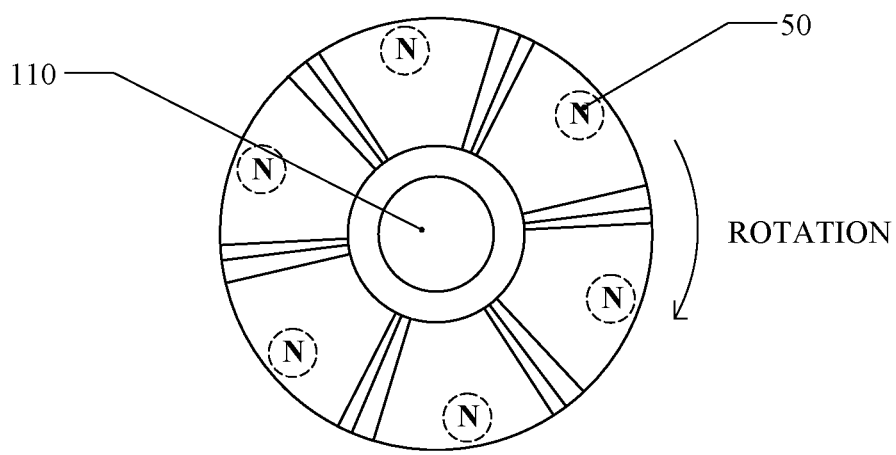
FIG. 6C shows a bottom plan view of the impeller of FIG. 6A.

The impeller 40 is illustrated in FIGS. 6A-6C as a semi-open type (e.g., having an end plate on one side of impeller). As such, the hydrodynamic bearing features 90 can be provided on or formed by an end plate on one side of the impeller 40. While the impeller 40 is illustrated as a semi-open type (e.g., having an end plate on one side of impeller), it will be understood that an impeller can be an open, pressure balanced type impeller to reduce axial thrust by omitting an end plate on both sides of the arc-shaped segments. As such, the hydrodynamic bearing features 90 can be formed on the arc-shaped segments even in the absence of an end plate. Suitable impellers include open type (e.g., no end plates on either side of an impeller), semi-open type (e.g., end plate on one side of an impeller), and closed type (e.g., end plate on both sides of an impeller). It will be further understood that other types of impellers may also be suitable, including other blade shapes and rotation in a different direction.

The force created by the axial hydrodynamic bearing acts to separate the impeller 40 from contacting the pump housing 30 during rotation. Additionally, the force created by the axial hydrodynamic bearing acts opposite to the attractive force created by some of impeller permanent magnets 50 and carrier permanent magnets 55. By combining the radial magnetic bearing formed by some of impeller permanent magnets 50 and carrier permanent magnets 55 with the axial hydrodynamic bearing formed by hydrodynamic bearing features 90 and bearing surface 120, impeller 40 is suspended within pump housing 30 with no contact.

The thickness of fluid gap 130 can be determined by the balance between the attractive force created by some of impeller permanent magnets 50 and carrier permanent magnets 55 and the opposing hydrodynamic force created by hydrodynamic bearing features 90 and bearing surface 120. Blood component damage is largely affected by shear stress, which in turn is governed by the fluid gap thickness in impeller bearings. Therefore, a large fluid gap is desirable to minimize trauma to blood components. In order to maximize the thickness of fluid gap 130, the axial force required to be generated by the hydrodynamic bearing formed between hydrodynamic bearing features 90 and bearing surface 120 should be minimized. However, the attractive force generated by some of impeller permanent magnets 50 and carrier permanent magnets 55 increases the force required from the axial hydrodynamic bearing due to the fact that the attractive magnetic forces must be sufficient to transmit enough torque to impeller 40 during rotation with a reasonable margin of safety. Otherwise, impeller 40 may cease to rotate with motor 70 if more torque is required than can be transmitted by the axial magnetic coupling. This is known as magnetic coupling slippage. Patient safety can be improved by avoiding magnetic coupling slippage.

In some embodiments, it may be desirable to reduce the force required from the axial hydrodynamic bearing formed by hydrodynamic bearing features 90 and bearing surface 120. Fluid pressure created by the rotation of impeller 40 in the impeller chamber can enter fluid gap 130. This extra pressure assists in axially separating impeller 40 from pump housing 30 during rotation and decreases the axial force required to be generated by the axial hydrodynamic bearing. In this manner, impeller 40 "self-levitates" using the pressure created by its own rotation. This can allow the thickness of fluid gap 130 to reach relatively large values and thereby reduces trauma and damage to blood components passing through the axial hydrodynamic bearing.

So that impeller 40 maintains a relatively stable axial position during operation, the axial forces generated by (1) impeller permanent magnets 50 and carrier permanent magnets 55, (2) hydrodynamic bearing features 90 and bearing surface 120, and (3) pressure generated by the rotation of impeller 40 that enters fluid gap 130, should all be balanced. Otherwise, impeller 40 may contact bearing surface 120 or the opposing surface of pump housing 30 during rotation. The force generated by pressure is equal to the pressure multiplied by the area upon which the pressure acts. Opening 110 on bottom of impeller 40 may be sized to adjust the area upon which pressure generated by the rotation of impeller 40 acts. In this way, the force generated by the pressure created by the rotation of impeller 40 may be adjusted, so that the axial forces acting on impeller 40 are balanced. Opening 110 may be of any size or shape, including circular, triangular, rectangular, square, or the like. Additionally, opening 110 may be comprised of multiple openings of any shape or size. However, in some embodiments, the cumulative size of opening 110 is not decreased to an extent that causes the axial force created by pressure caused by rotation of the impeller to exceed the attractive axial force of impeller permanent magnets 50 and carrier permanent magnets 55 under any operating condition, otherwise impeller 40 may contact pump housing 30 under such operating condition. The opening 110 can be smaller than a closest distance between any two radially opposite arc-shaped segments.

It will be recognized that any rotating body possesses angular momentum due to the product of its rotating inertia and speed. Conservation of angular momentum can assist in providing stable rotation of a body by resisting forces which would tend to angularly misalign the rotational axis from the principle geometric axis. Such misalignment can lead to wobble or other undesirable effects. The stabilizing force of a rotating mass is commonly referred to as a gyroscopic force due to its use in gyroscopes. As an impeller begins to increase rotational speed and levitate, unbalanced forces acting on the impeller may cause wobble or tilting leading to unstable rotation. If the rotational speed is further increased, thereby increasing angular momentum, gyroscopic force may begin to counteract the wobble. If rotational speed continues to increase, any wobble may be effectively reduced to an acceptable amplitude. Conversely, the angular momentum of the impeller may be effectively increased by increasing rotational inertia without increasing speed. This can be accomplished by removing material from inside the blades and placing a smaller volume of high density material, such as tungsten, near the outer periphery of the blades. In doing so, the rotational inertia can be increased without significantly increasing the overall weight of the impeller.

Figure 7A:
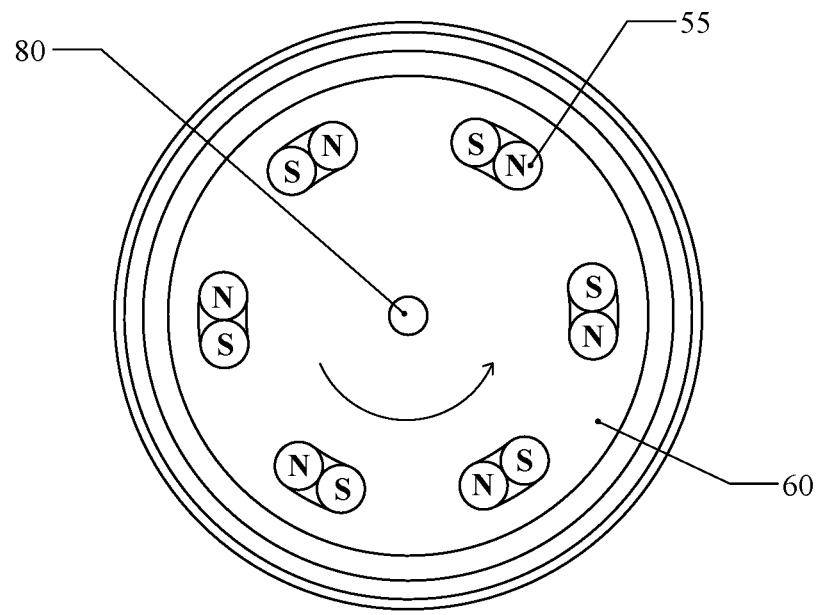
FIG. 7A shows top plan view of an illustrative embodiment of a motor and carrier.
Figure 7B:
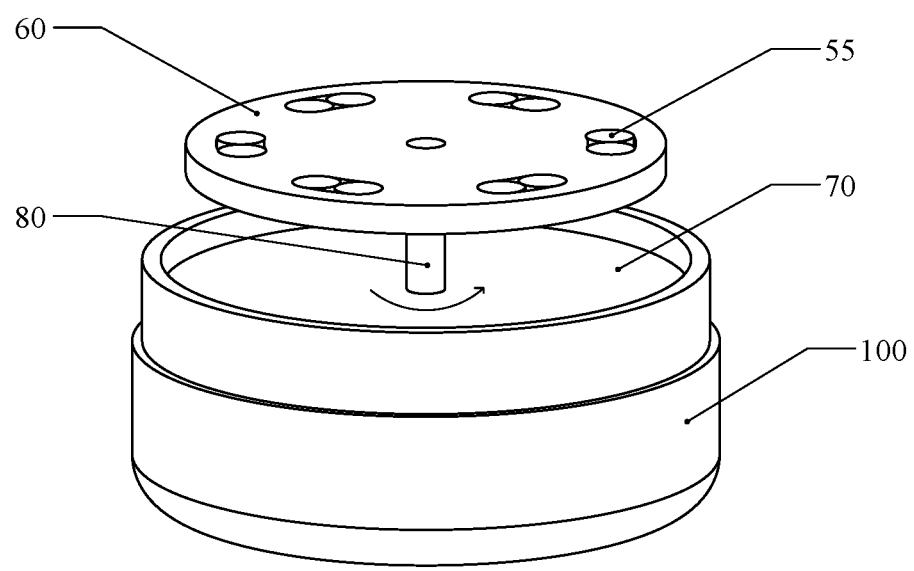
FIG. 7B shows a perspective view of the motor and carrier of FIG. 7A.

In order to increase the torque transmission capability of the axial magnetic coupling formed between impeller permanent magnets 50 and carrier permanent magnets 55 without appreciably increasing the attractive axial force between impeller permanent magnets 50 and carrier permanent magnets 55, carrier permanent magnets 55 contained in carrier 60 may be comprised of magnet pairs as shown in FIGS. 7A and 7B. As shown in FIGS. 7A and 7B, the individual magnets in each pair may be arranged with different magnetic polarities. For example, the carrier permanent magnets 55 comprise pairs of adjacent magnets that are oriented to have different magnetic polarities. Each pair comprises a first magnet attractively coupled to a corresponding impeller permanent magnet 50 and a second magnet repelling the corresponding impeller permanent magnet 50. The number of pairs of carrier permanent magnets 55 can be equal to the number of impeller permanent magnets 50. In this manner, the impeller permanent magnets 50 within impeller 40 may experience both an attractive force and a repelling force both acting in the same direction tangential to the radius of impeller 40 as carrier 60 rotates. This in effect multiplies the force acting to rotate impeller 40 and increases the torque capability of the axial magnetic coupling. As the carrier 60 rotates, the carrier permanent magnet 55 attracting the corresponding impeller permanent magnet 50 can lead in front of the carrier permanent magnet 55 that repels the corresponding impeller permanent magnet 50. Accordingly, the carrier permanent magnet 55 that repels the corresponding impeller permanent magnet 50 can repulsively urge the corresponding impeller permanent magnet 50 from behind. Because the second magnets of each magnet pair contained within carrier 60 create a repulsive axial force on impeller permanent magnets 50, the net attractive axial force created between impeller permanent magnets 50 and carrier permanent magnets 55 is largely unchanged compared to single magnets located within carrier 60. The opposing force required to be generated by the axial hydrodynamic bearing formed between hydrodynamic bearing features 90 and bearing surface 120 is also largely unchanged even with the increased torque capability of the permanent magnet arrangement shown in FIG. 7. Other additional permanent magnets may be contained within carrier 60 to further enhance axial or radial forces acting on impeller permanent magnets 50 to further increase torque transmission capability, radial magnetic bearing stiffness, or both.

Referring now to FIGS. 8-15B, some embodiments of the blood pump can include magnetic couplings to provide both radial and axial support to a rotating impeller. At least some of the features discussed with respect to the embodiments shown in FIGS. 1-7 can be applied to the embodiments shown in FIGS. 8-15B.

Figure 8:
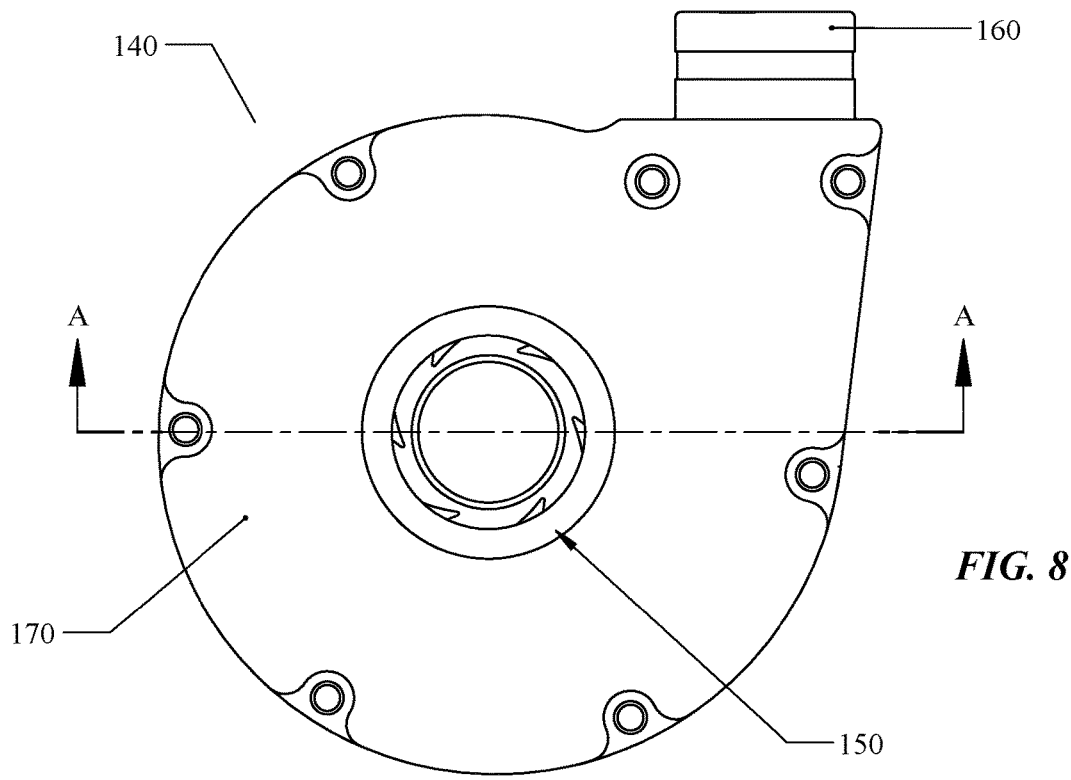
FIG. 8 shows a top view of an illustrative embodiment of a pump.
Figure 9:
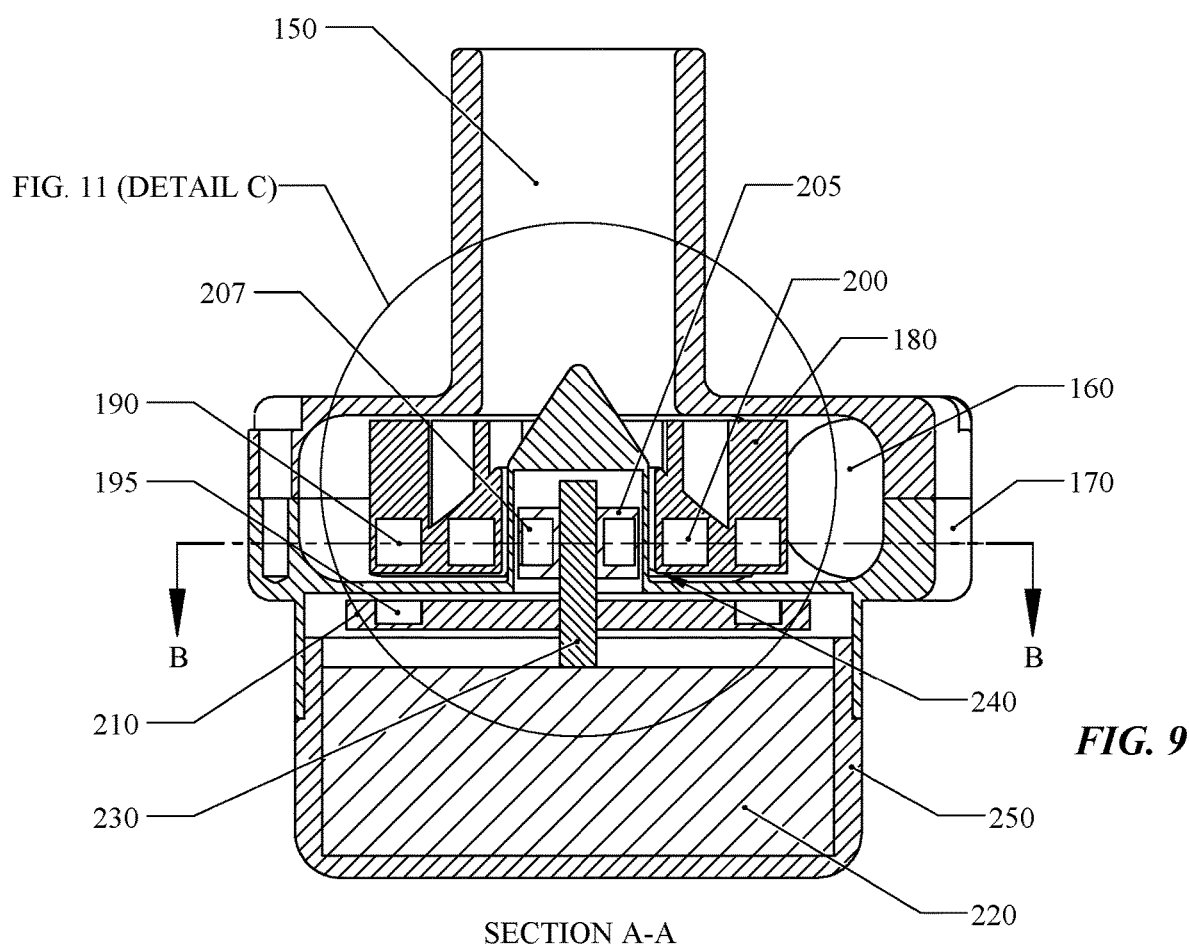
FIG. 9 shows a cross-sectional side view of the pump taken along section lines A-A of FIG. 8.

A pump 140 is shown in FIG. 8 and FIG. 9. The pump 140 allows large clearances between pump housing 170 and impeller 180 to exist during operation. Similar or like items can perform the same function as pump 5 shown in FIG. 1 and FIG. 2, and the features of such items are not all discussed hereafter, for brevity. Impeller radial permanent magnets 200 and rotor hub radial permanent magnets 207 can be used to provide additional torque transmission capability as well as provide additional axial restraint of impeller 180. The pump 140 can comprise a motor 220, a rotor 202 comprising a rotor hub 205 and a carrier 210 and, a shaft 230. Carrier 210 and/or hub 205 can be separate, joined, integral, or unitary to form rotor 202. Hub 205 contains one or more permanent magnets and/or magnetic materials. Motor 220 rotates rotor 202 (e.g., via shaft 230) causing rotor radial permanent magnets 207 placed in hub 205 to rotate.

Figure 12A:
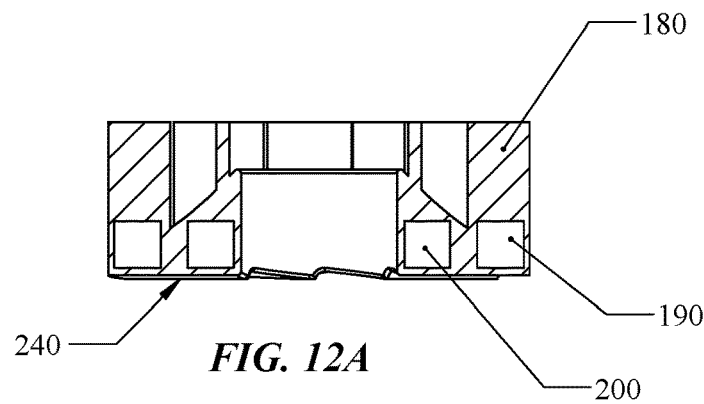
FIG. 12A shows a cross-sectional view of an impeller.
Figure 12B:
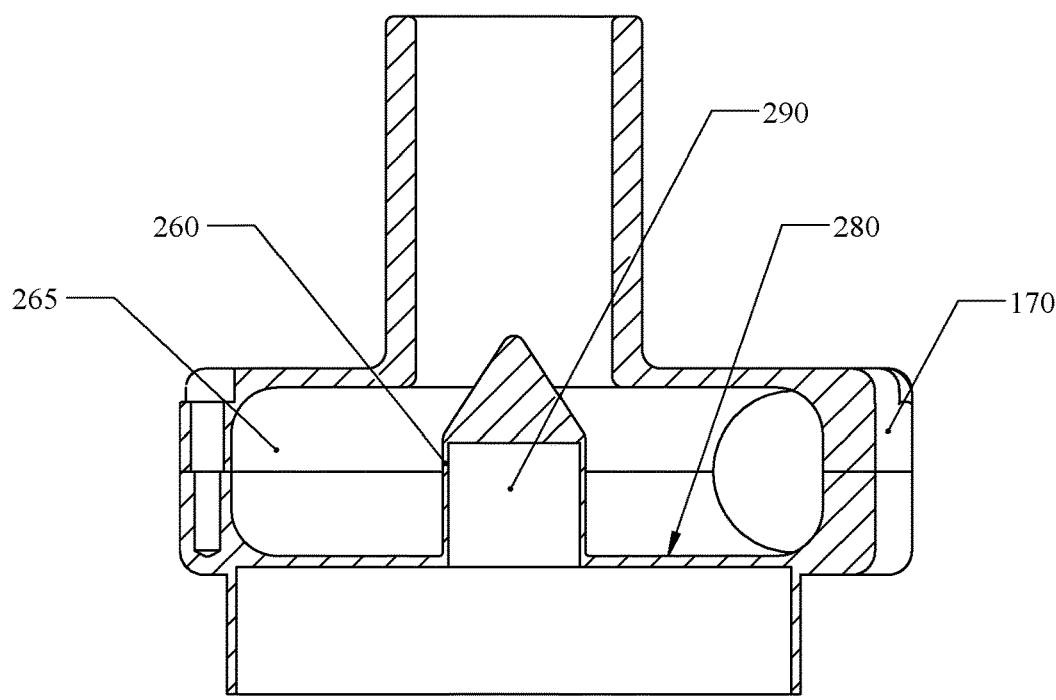
FIG. 12B shows a cross-sectional view of an illustrative embodiment of a pump housing.
Figure 12C:
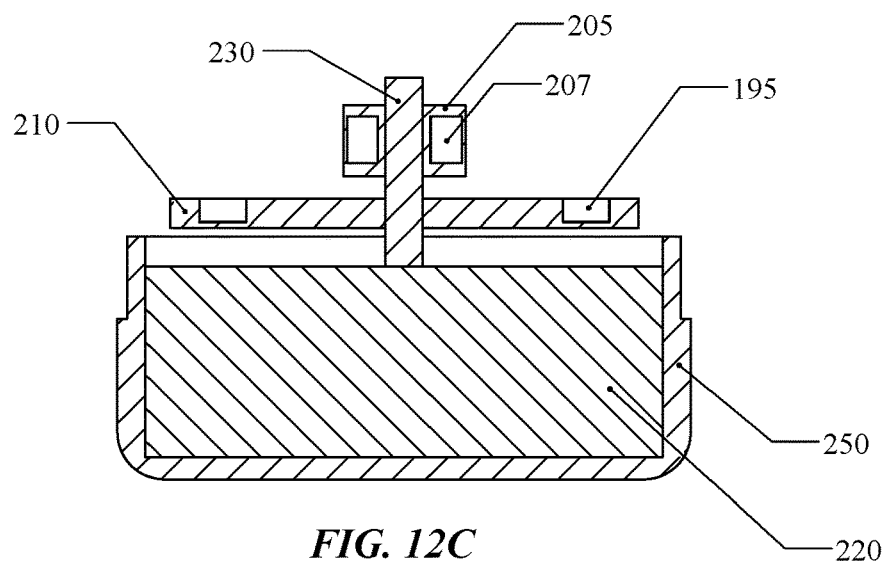
FIG. 12C shows a cross-sectional view of an illustrative embodiment of a motor and motor housing.
Figure 13A:
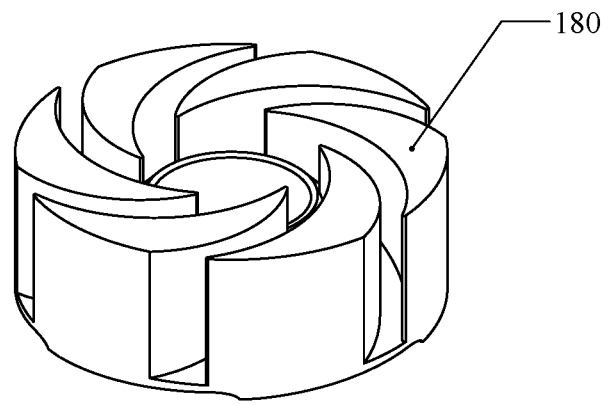
FIG. 13A shows a top perspective view of an illustrative embodiment of an impeller.
Figure 13B:
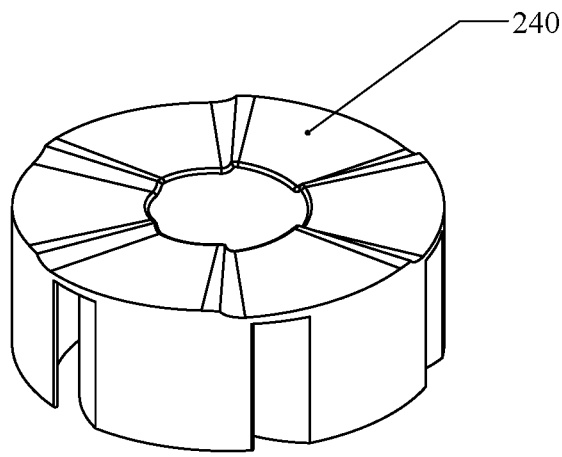
FIG. 13B shows a bottom perspective view of the impeller of FIG. 13A.
Figure 13C:
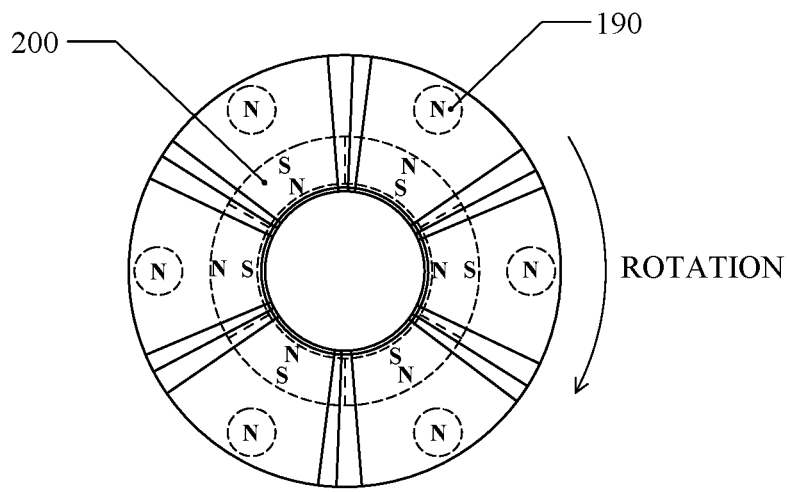
FIG. 13C shows a bottom plan view of the impeller of FIG. 13A.

A cross-sectional view of an illustrative embodiment of pump housing 170 without impeller 180 is shown in FIGS. 12A-12C. Pump housing 170 may provide a non-ferromagnetic and/or non-electrically conductive diaphragm 260 separating impeller chamber 265 from the chamber housing the motor. Diaphragm 260 defines cavity 290 providing a region for hub 205 to rotate within. Impeller 180 includes one or more permanent magnets and/or magnetic materials. Impeller radial permanent magnets 200 allow impeller 180 to be magnetically coupled to hub 205. This radial magnetic coupling allows motor 220 to cause impeller 180 to rotate when motor 220 rotates hub 205. Rotor radial permanent magnets 207 in hub 205 and impeller radial permanent magnets 200 in impeller 180 form a radial magnetic coupling between the impeller 180 and hub 205. The radial attractive force of the magnetic coupling formed by impeller radial permanent magnets 200 and rotor radial permanent magnets 207 also provide additional axial restraint of impeller 180. For example, axial movement of impeller 180 would misalign impeller radial permanent magnets 200 and rotor radial permanent magnets 207 axially. The attractive magnetic forces of impeller radial permanent magnets 200 and rotor radial permanent magnets 207 would restrain impeller 180 in the axial direction. Because of the magnetic forces created by impeller radial permanent magnets 200 and rotor radial permanent magnets 207, axial movement of impeller 180 may cause axial force to be exerted on shaft 230 and hub 205 of motor 220, which is then transferred to bearing(s) (not shown) of motor 220.

Figure 10:
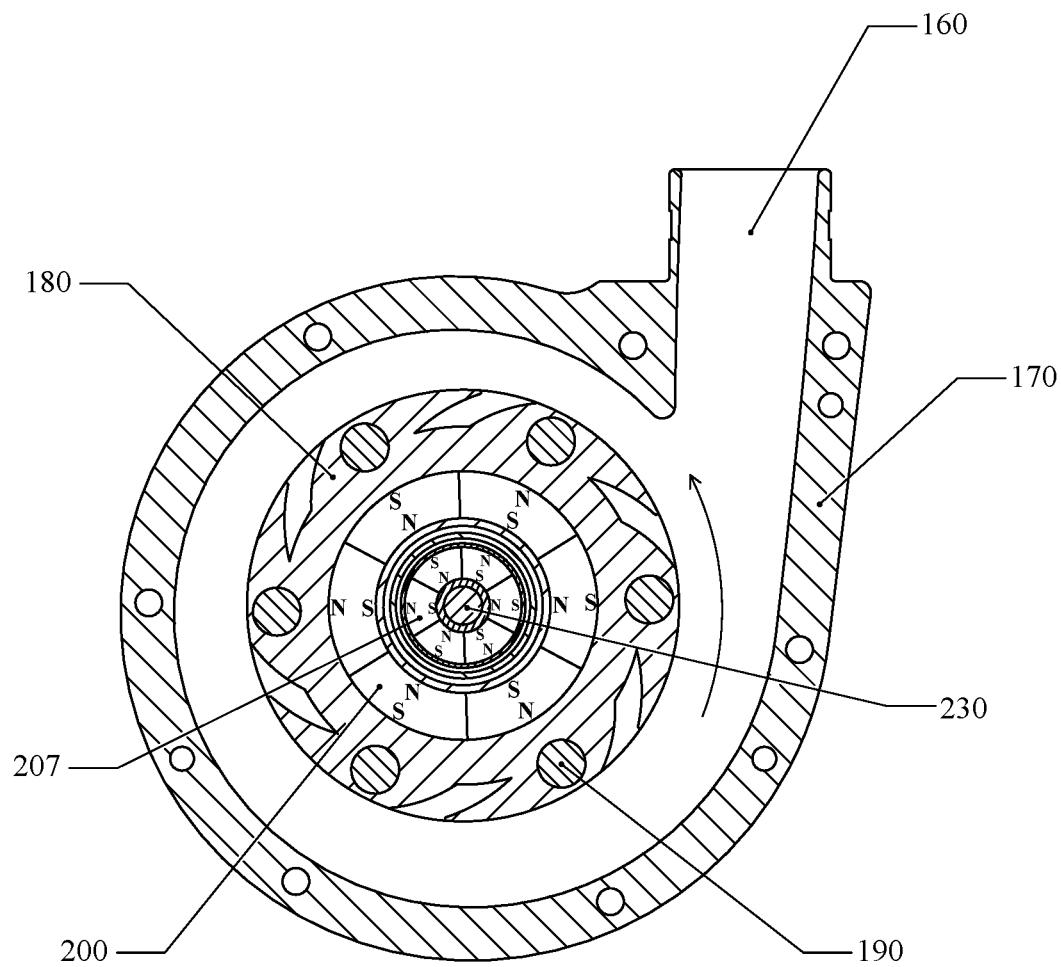
FIG. 10 shows a cross-sectional top view of the pump taken along section lines B-B of FIG. 9.
Figure 11:
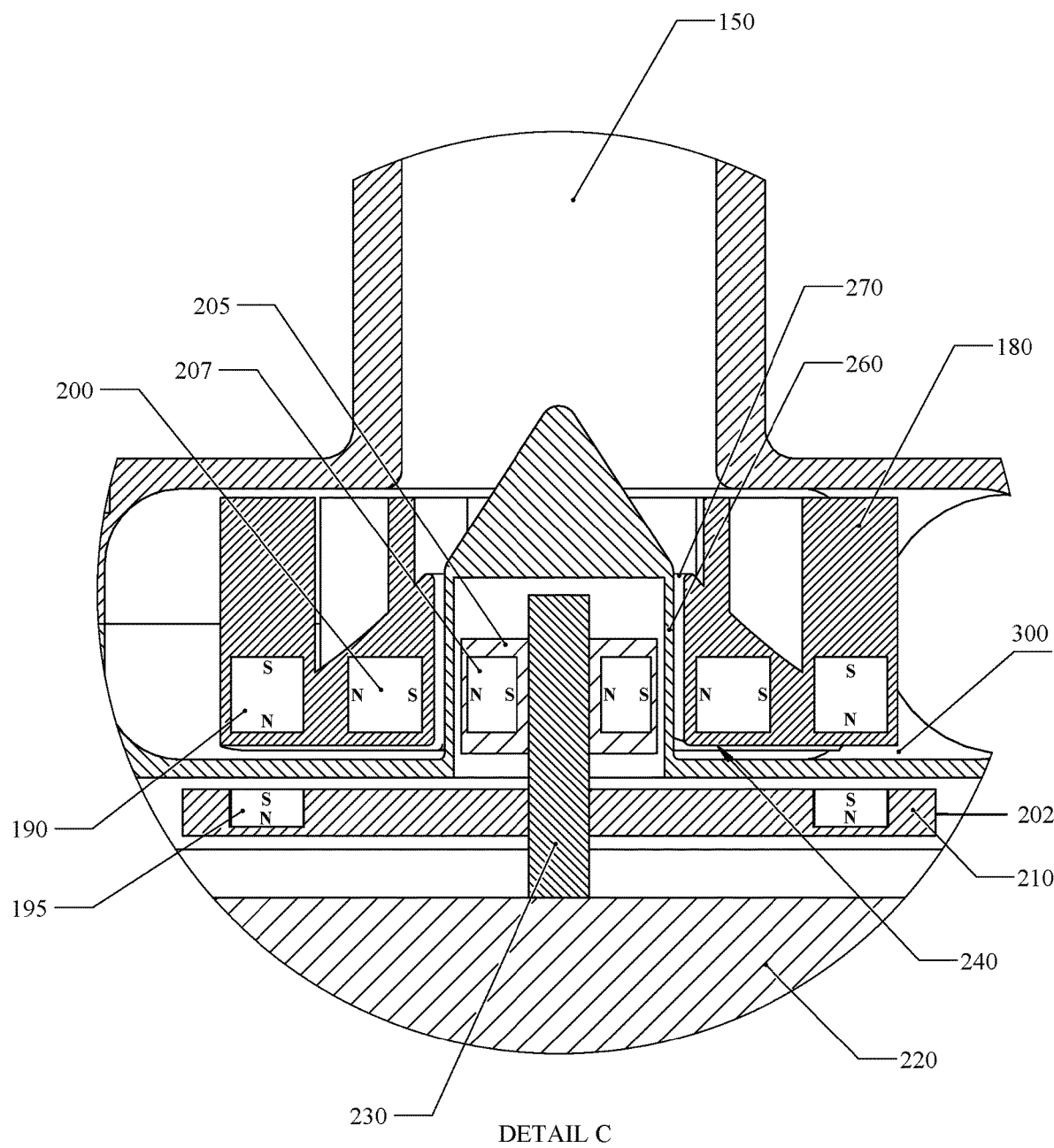
FIG. 11 shows an enlarged cross-sectional side view of the pump of section C of FIG. 9.

While impeller radial permanent magnets 200 and rotor radial permanent magnets 207 are shown as arc-shaped like quadrants of a cylinder in FIG. 10, it will be recognized that impeller radial permanent magnets 200 and rotor radial permanent magnets 207 may be shaped in a variety of different manners to provide the radial magnetic coupling. For example, one or more ring-shaped magnets, square/rectangular-shaped magnets, bar-shaped, or the like may be utilized.

Impeller axial permanent magnets 190 and rotor axial permanent magnets 195 still provide torque transmission capability as well as radial restraint of the impeller during rotation. The radial restoring forces generated by impeller axial permanent magnets 190 and rotor axial permanent magnets 195 may be sufficient to overcome any radial forces created by the attraction of impeller radial permanent magnets 200 and rotor radial permanent magnets 207. In doing so, no further radial restraint, such as would be provided by a radial hydrodynamic bearing, may be required. This can allow a large radial bearing gap 270 of greater than 0.005" to exist between impeller 180 and diaphragm 260 resulting in minimal shear stress exerted on blood components passing through radial bearing gap 270. For example, the radial bearing gap 270 can be greater than 0.005", 0.010", 0.015", or 0.020". Optionally, the radial bearing gap 270 can form a hydrodynamic bearing with a hydrodynamic bearing feature, for example on the diaphragm 260 and/or the impeller 180; however, such a hydrodynamic bearing is not required for radial stability of the impeller 180, and the radial bearing gap 270 can be sufficiently large to avoid hydrodynamic bearing effects therein.

Impeller 180 may provide hydrodynamic bearing features 240 on its bottom surface or surfaces to form an axial hydrodynamic bearing with bearing surface 280. Hydrodynamic bearing features 240 may be ramps, wedges, steps, grooves or any other feature that creates hydrodynamic pressure during rotation.

Hydrodynamic bearing features 240 on the bottom of impeller 180 act to create a hydrodynamic bearing and may separate impeller 180 from bearing surface 280 of pump housing 170 during rotation. However, pressure caused by the rotation of impeller 180 also acts to lift impeller 180 off of bearing surface 280. If these pressure forces become too great, impeller 180 would be pushed to the opposite side of pump housing 170 and make contact, potentially leading to hemolysis or other blood trauma. Therefore, with respect to the pump 5, described above, the attractive axial forces generated by impeller permanent magnets 50 and carrier permanent magnets 55 are not to be exceeded by the axial forces generated by hydrodynamic bearing features 90 and the pressure created by impeller rotation. The size of the fluid gap 130 existing under impeller 40 during rotation is controlled accordingly.

With respect to the pump 140, the attractive forces of impeller axial permanent magnets 190 and rotor axial permanent magnets 195 may be made weaker to allow the pressure created during rotation of impeller 180 to further counteract the attractive forces of impeller axial permanent magnets 190 and rotor axial permanent magnets 195 and allow impeller 180 to lift off bearing surface 280 even further during operation, thereby increasing axial bearing gap 300 and reducing fluid shear stress. The axial restraint of the radial coupling formed by impeller radial permanent magnets 200 and rotor radial permanent magnets 207 would then begin restraining the impeller in the axial direction and prevent impeller contact with the opposing side of pump housing 170 and may result in a larger axial bearing gap 300 of greater than 0.005" to reduce fluid shear stress. In this way, the axial magnetic coupling formed between impeller axial permanent magnets 190 and rotor axial permanent magnets 195 and the radial magnetic coupling formed by impeller radial permanent magnets 200 and rotor radial permanent magnets 207 would both act to restrain impeller 180 in the axial direction and may allow the axial bearing gap 300 to be larger during rotation than would be possible without the radial coupling formed by impeller radial permanent magnets 200 and rotor radial permanent magnets 207.

Figure 14A:
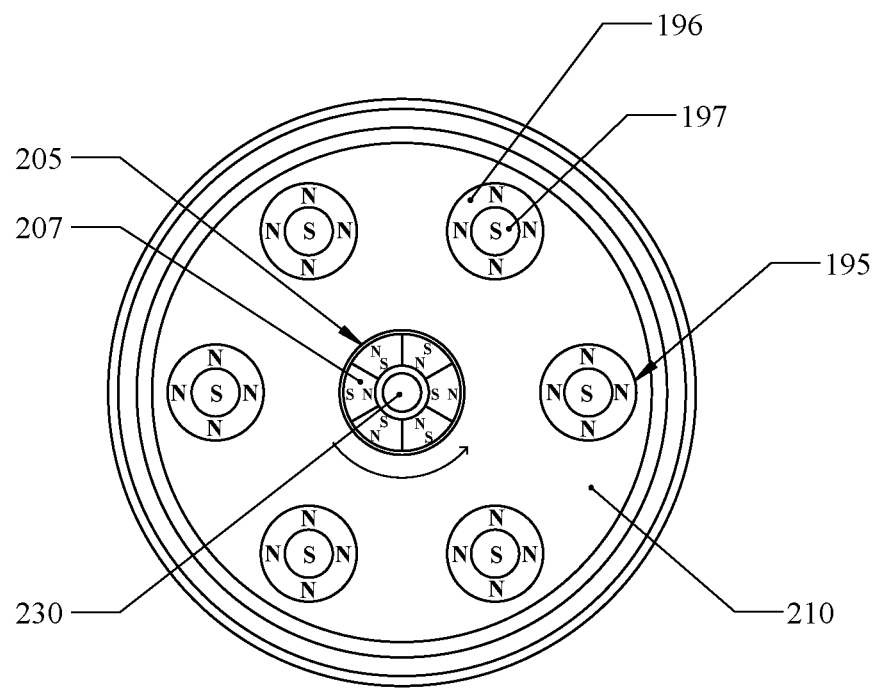
FIG. 14A shows top plan view of an illustrative embodiment of a motor and carrier.
Figure 14B:
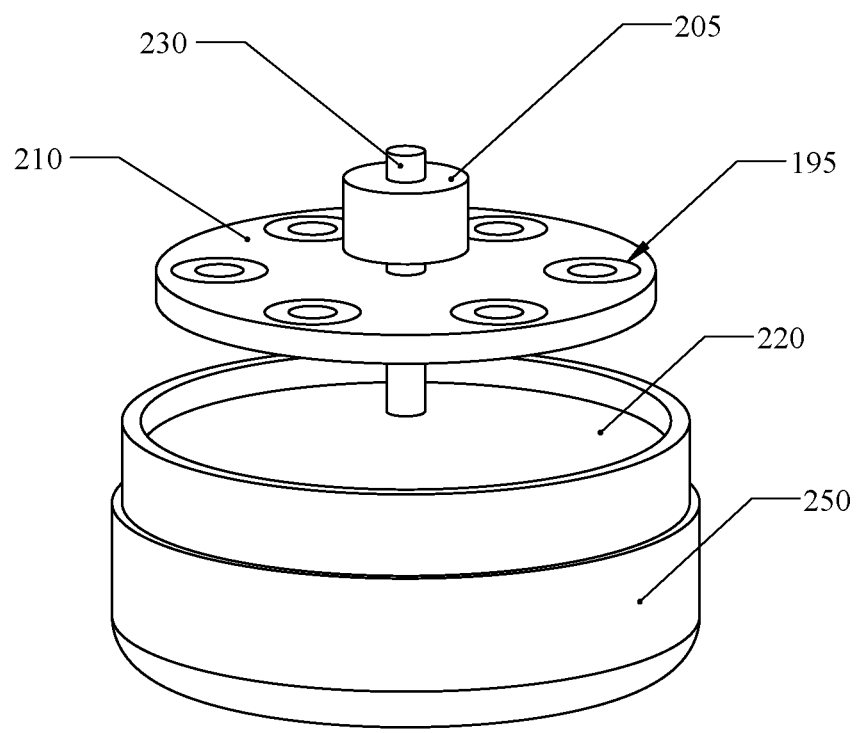
FIG. 14B shows a perspective view of the motor and carrier of FIG. 14A.

By generating relatively weaker attractive axial forces between impeller axial permanent magnets 190 and rotor axial permanent magnets 195 to allow a larger axial bearing gap 300 during operation, the radial restoring forces of impeller axial permanent magnets 190 and rotor axial permanent magnets 195 may be reduced as well, potentially allowing impeller 180 to contact diaphragm 260 during operation. To help mitigate this possibility, a magnet arrangement is shown in FIGS. 14A and 14B. One or more of the rotor axial permanent magnets 195 can include two individual permanent magnets, such as outer permanent magnet 196 and inner permanent magnet 197. Outer permanent magnet 196 may be ring-shaped (e.g., circular, polygonal, or another shape) with inner permanent magnet 197 residing within outer permanent magnet 196. Both outer permanent magnet 196 and inner permanent magnet 197 are axially magnetized, but are assembled with opposite polarity (i.e., opposite magnetic field orientation) in the axial direction. The magnetic field of outer permanent magnet 196 acts to suppress the magnetic field of inner permanent magnet 197 because of the opposing polarity (i.e., opposite magnetic field orientation) and thereby significantly reduces the axial attractive force with impeller axial permanent magnet 190 contained within impeller 180. Reductions in axial force of about 50% have been shown by testing. However, further testing has shown that this magnet arrangement does not reduce the radial restoring force generated by impeller axial permanent magnets 190 and rotor axial permanent magnets 195 near as much with a loss of only about 20% shown during testing. This is due to the radial repulsive force generated between impeller axial permanent magnets 190 and outer permanent magnets 196. As impeller 180 is radially pushed by fluid pressure forces caused by impeller rotation, the impeller 180 can be restrained in the radial direction by radial magnetic forces generated from (1) attraction between impeller axial permanent magnets 190 and inner permanent magnets 197 and (2) repulsion between impeller axial permanent magnets 190 and outer permanent magnets 196. Therefore, the permanent magnet arrangement shown in FIGS. 14A and 14B can allow a significant increase in the size of axial bearing gap 300 while still providing sufficient axial and radial restraint of impeller 180. This alternate embodiment may allow relatively large radial bearing gap 270 and axial bearing gap 300 of greater than 0.005" to exist during operation and result in reduced blood trauma as compared to bearing gaps created by hydrodynamic bearings alone.

Figure 15A:
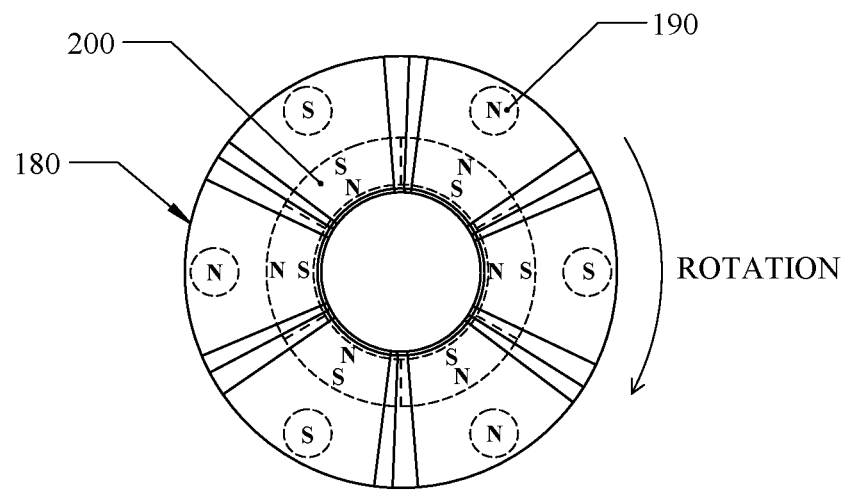
FIG. 15A shows a bottom plan view of an illustrative embodiment of an impeller.
Figure 15B:
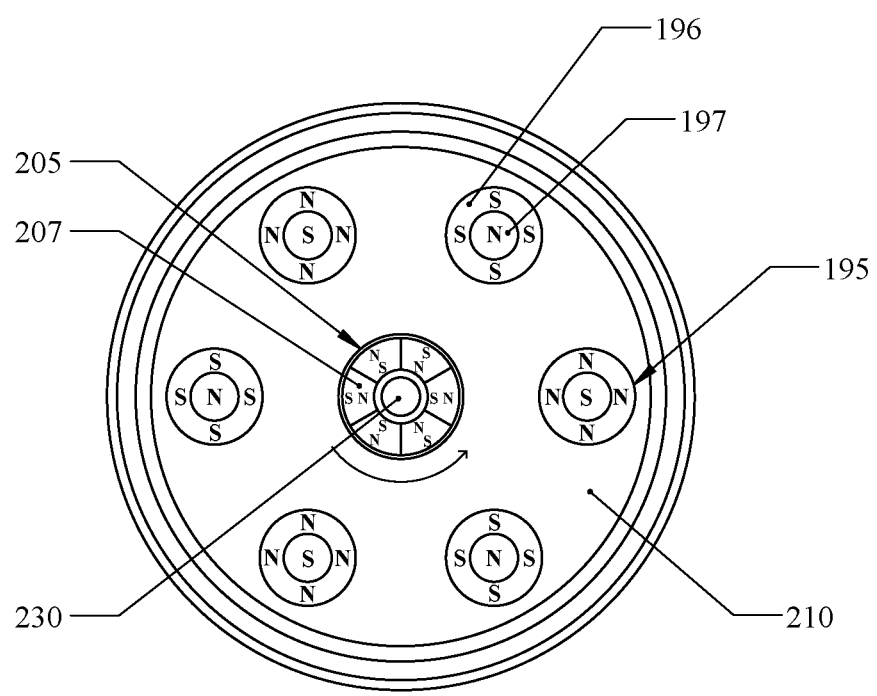
FIG. 15B shows a top plan view of an illustrative embodiment of a carrier.

The net attractive force between impeller 180 and carrier 210 can be further reduced, without decreasing radial restoring forces, by employing an alternating polarity (i.e., alternating magnetic field orientation) arrangement as shown in FIGS. 15A and 15B. In this configuration, impeller axial permanent magnets 190 and inner permanent magnets 197 are still attracting in the axial direction to maintain torque transmission capacity, but they now have alternating polarities as shown in FIGS. 15A and 15B. Outer permanent magnets 196 also alternate polarity (i.e., alternating magnetic field orientation) correspondingly and are arranged to repulse from impeller radial permanent magnets 200 in both the axial and radial direction. These repulsion forces further lower the net attractive force pulling impeller 180 down towards bearing surface 280 allowing an even larger axial bearing gap 300 to exist during rotation. The same repulsion forces created by outer permanent magnets 196 interacting with impeller radial permanent magnets 200 can also serve to further increase the radial restoring forces resisting impeller movement in the radial direction due to fluid pressure caused by impeller rotation and thereby can beneficially allow an even larger radial bearing gap 270 to exist during rotation.

In some embodiments, no additional mechanism is required to radially or axially stabilize the impeller 180 during rotation. For example, in some embodiments, only the attracting impeller axial permanent magnets 190 and rotor axial permanent magnets 195 can provide radial stability and the attracting impeller radial permanent magnets 200 and rotor radial permanent magnets 207 along with pressure forces created by impeller rotation can provide axial stability to the impeller 180. In some embodiments, no hydrodynamic bearing is required radially spaced apart from or within the impeller 180. In some embodiments, no support structure is required radially spaced apart from or within the impeller 180, for example, to form a hydrodynamic bearing. In some embodiments, gyroscopic forces may be used to provide angular stability as previously described.

Figure 16:
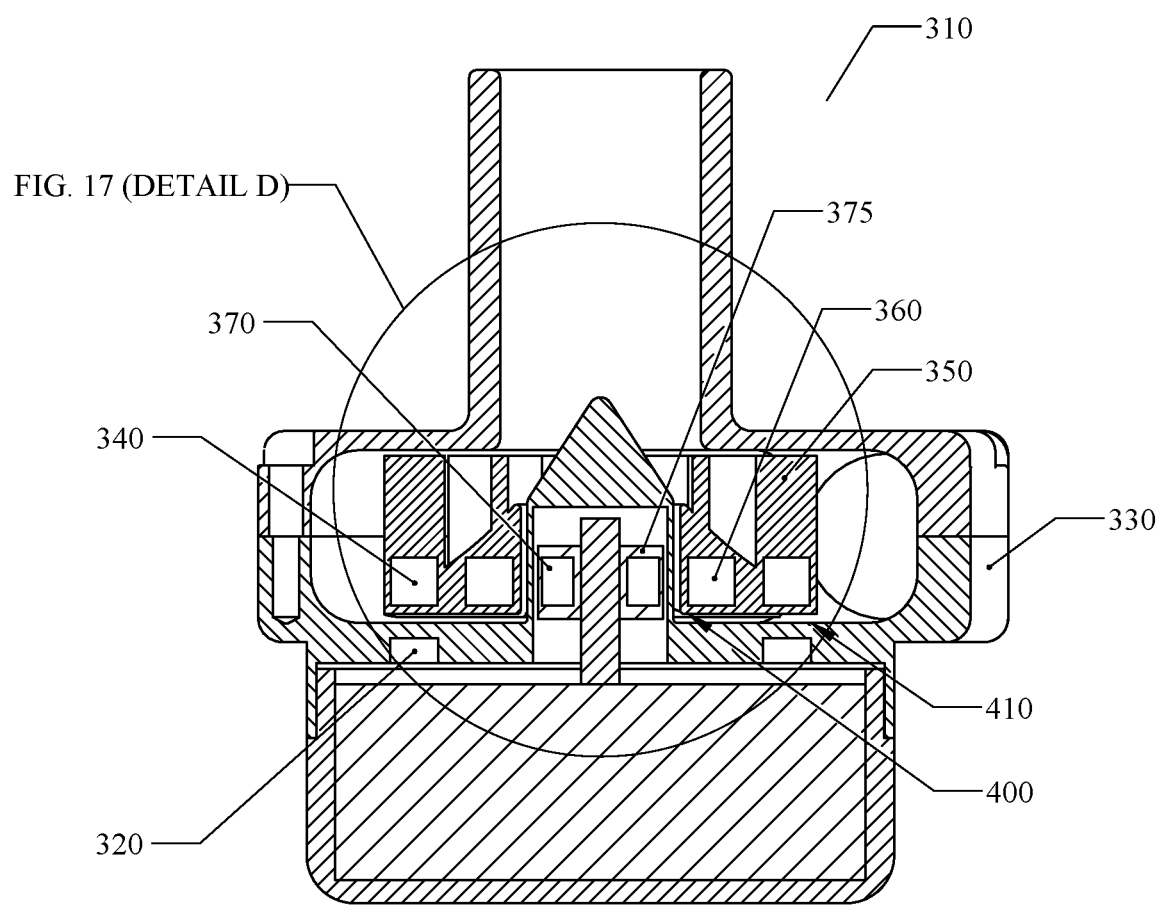
FIG. 16 shows a cross-sectional side view of an illustrative embodiment of a pump.
Figure 17:
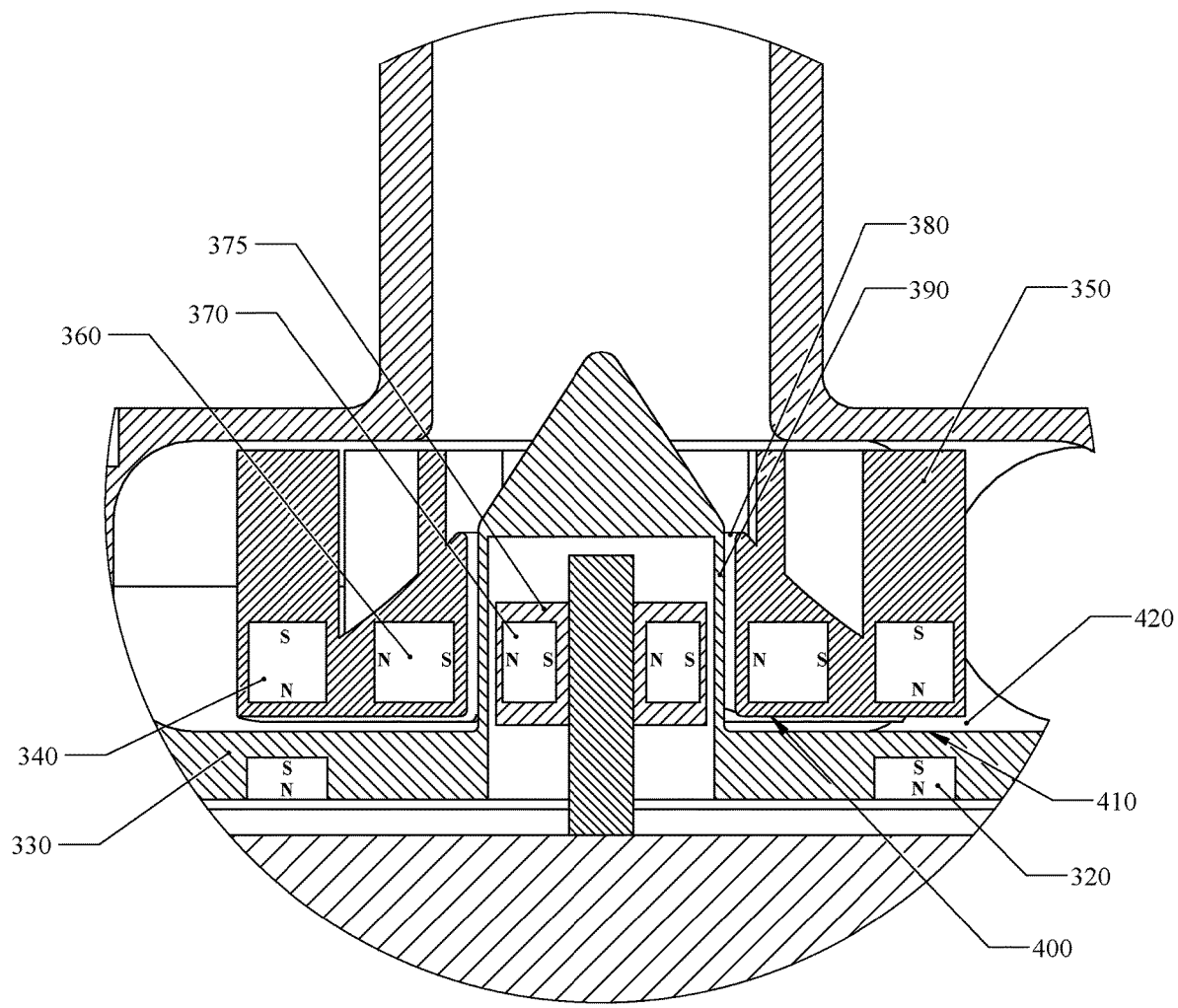
FIG. 17 shows an enlarged cross-sectional side view of the pump of section D of FIG. 16.

Referring now to FIGS. 16-17, some embodiments of the blood pump can include a magnetic coupling to provide axial support to a rotating impeller and a magnetic bearing to provide radial support. At least some of the features discussed with respect to the embodiments shown in FIGS. 8-15B can be applied to the embodiments shown in FIGS. 16-17.

A pump 310 is shown in FIG. 16. The pump 310 replaces the axial magnetic coupling of pump 140 with a permanent magnetic bearing formed between non-rotating housing axial permanent magnet 320 placed in pump housing 330 and impeller axial permanent magnets 340 to provide radial restraint of impeller 350. The housing axial permanent magnet 320 can be ring-shaped or formed by a series of similarly polarized magnets that form a continuous magnetic field. Similar or like items can perform the same function as pump 140 shown in FIGS. 9-12, and the features of such items may not all be discussed hereafter, for brevity. Housing axial permanent magnet 320 may be a single magnet or include multiple magnets placed in a variety of arrangements to produce the required radial restoring forces while minimizing axial attractive forces. For example, another housing ring magnet may be placed outside or inside housing ring magnet 320 to enhance radial magnetic bearing stiffness and/or diminish axial attraction forces. The radial restoring forces generated by housing axial permanent magnet 320 and impeller axial permanent magnets 340 may be sufficient to overcome any radial forces created by the attraction of impeller radial permanent magnets 360 and rotor hub radial permanent magnets 370 located in rotor hub 375. In doing so, no further radial restraint, such as would be provided by a radial hydrodynamic bearing, may be required. This can allow a large radial bearing gap 380 of greater than 0.005" to exist between impeller 350 and diaphragm 390 as shown in FIG. 17 resulting in minimal shear stress exerted on blood components passing through radial bearing gap 380. For example, the radial bearing gap 380 can be greater than 0.005", 0.010", 0.015", or 0.020". Optionally, the radial bearing gap 380 can form a hydrodynamic bearing with a hydrodynamic bearing feature, for example on the diaphragm 390 and/or the impeller 350; however, such a hydrodynamic bearing is not required for radial stability of the impeller 350, and the radial bearing gap 380 can be sufficiently large to avoid hydrodynamic bearing effects therein.

Impeller 350 may provide hydrodynamic bearing features 400 on its bottom surface or surfaces to form an axial hydrodynamic bearing with bearing surface 410 shown in FIG. 17. Hydrodynamic bearing features 400 may be ramps, wedges, steps, grooves or any other feature that creates hydrodynamic pressure during start-up to oppose the attractive force of housing axial permanent magnet 320 and impeller axial permanent magnets 340 thereby levitating the impeller. With respect to the pump 310, the pressure created during rotation of impeller 350 may allow impeller 350 to lift off bearing surface 410 even further during operation, thereby increasing axial bearing gap 420 and reducing fluid shear stress. The axial restraint of the radial coupling formed by impeller radial permanent magnets 360 and rotor hub radial permanent magnets 370 would then begin restraining the impeller in the axial direction and prevent impeller contact with the opposing side of pump housing 330 and may result in a larger axial bearing gap 420 of greater than 0.005" to reduce fluid shear stress.

Embodiments disclosed herein include:

A. A blood pump comprising: a pump housing having an inlet, an outlet, a first chamber, and a second chamber; a carrier within the first chamber, the carrier being rotatable by a motor and comprising carrier permanent magnets; and an impeller within the second chamber and comprising: impeller permanent magnets that are axially spaced apart from and magnetically coupled to the carrier permanent magnets; and B. A method of pumping blood, the method comprising: with a motor, rotating a carrier within a first chamber of a pump housing, the carrier comprising carrier permanent magnets; with the carrier, rotating an impeller within a second chamber of the pump housing, the impeller comprising impeller permanent magnets that are axially spaced apart from and forming a magnetic coupling with the carrier permanent magnets; radially stabilizing the impeller with the magnetic coupling; and axially stabilizing the impeller with a hydrodynamic bearing feature on a side of the impeller facing the carrier.

C. A blood pump comprising: a pump housing having an inlet, an outlet, a first chamber, and a second chamber; a rotor within the first chamber, the rotor being rotatable by a motor and comprising: rotor axial permanent magnets; and rotor radial permanent magnets; and an impeller within the second chamber and comprising: impeller axial permanent magnets that are axially spaced apart from and magnetically coupled to the rotor axial permanent magnets; and impeller radial permanent magnets that are radially spaced apart from and magnetically coupled to the rotor radial permanent magnets.

D. A method of pumping blood, the method comprising: with a motor, rotating a rotor within a first chamber of a pump housing, the rotor comprising rotor axial permanent magnets and rotor radial permanent magnets; with the rotor, rotating an impeller within a second chamber of the pump housing, the impeller comprising impeller axial permanent magnets and impeller radial permanent magnets; and radially stabilizing the impeller with an axial magnetic coupling between the impeller axial permanent magnets and the rotor axial permanent magnets; and axially stabilizing the impeller with a radial magnetic coupling between the impeller radial permanent magnets and the rotor radial permanent magnets.

E. A blood pump comprising: a pump housing having an inlet, an outlet, a first chamber, a second chamber, and a housing axial permanent magnet; a rotor hub within the first chamber, the rotor hub being rotatable by a motor and comprising rotor hub radial permanent magnets; and an impeller within the second chamber and comprising: impeller axial permanent magnets that are axially spaced apart from and magnetically attracted to the housing axial permanent magnet; and impeller radial permanent magnets that are radially spaced apart from and magnetically coupled to the rotor hub radial permanent magnets.

F. A method of pumping blood, the method comprising: with a motor, rotating a rotor hub within a first chamber of a pump housing, the rotor hub comprising rotor radial permanent magnets; with the rotor hub, rotating an impeller within a second chamber of the pump housing, the impeller comprising impeller axial permanent magnets and impeller radial permanent magnets; radially stabilizing the impeller with a permanent magnetic bearing formed between the impeller axial permanent magnets and a housing axial permanent magnet residing within the pump housing; and axially stabilizing the impeller with a radial magnetic coupling between the impeller radial permanent magnets and the rotor radial permanent magnets.

Each of embodiments A, B, C, D, E, and F may have one or more of the following additional elements in any combination:

Element 1: A hydrodynamic bearing feature on a side of the impeller facing the carrier.

Element 2: The hydrodynamic bearing feature is positioned between the impeller permanent magnets and the carrier permanent magnets.

Element 3: The impeller is configured to be axially supported during rotation by a balance of: an axial magnetic coupling between the impeller permanent magnets and the carrier permanent magnets; and a hydrodynamic force provided by the hydrodynamic bearing feature.

Element 4: The impeller is configured to be radially supported during rotation by an axial magnetic coupling between the impeller permanent magnets and the carrier permanent magnets.

Element 5: The impeller is radially stabilized solely with an axial magnetic coupling.

Element 6: The impeller is configured to be radially supported during rotation by a permanent magnetic bearing formed between the impeller permanent magnets and the housing axial permanent magnet.

Element 7: The impeller is radially stabilized solely with a radial magnetic bearing.

Element 8: The impeller defines an opening that extends axially through an entire height of the impeller, wherein no portion of the pump housing is within the opening.

Element 9: The carrier permanent magnets comprise pairs of adjacent magnets that are oriented to have different magnetic polarities, wherein each pair comprises a first magnet attractively coupled to a corresponding impeller permanent magnet and a second magnet repelling the corresponding impeller permanent magnet.

Element 10: Each of the rotor axial permanent magnets comprises: an outer permanent magnet; and an inner permanent magnet extending axially within an interior of the outer permanent magnet, the inner permanent magnet having a magnetic field orientation that is opposite a magnetic field orientation of the outer permanent magnet.

Element 11: The rotor radial permanent magnets, the impeller axial permanent magnets, and the impeller radial permanent magnets are mutually aligned with a position along an axis of the blood pump.

Element 12: The rotor axial permanent magnets are axially offset from the rotor radial permanent magnets.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A blood pump comprising:
   a pump housing having an inlet, an outlet, a first chamber, a second chamber, and a housing axial permanent magnet;
   a rotor hub within the first chamber, the rotor hub being rotatable by a motor and comprising rotor hub radial permanent magnets; and
   an impeller within the second chamber and comprising:
   impeller axial permanent magnets that are axially spaced apart from and magnetically attracted to the housing axial permanent magnet; and
   impeller radial permanent magnets that are radially spaced apart from and magnetically coupled to the rotor hub radial permanent magnets.

2. The blood pump of claim 1, wherein the impeller is configured to be axially supported during rotation by a balance of:
   a permanent magnetic bearing between the impeller axial permanent magnets and the housing axial permanent magnet;
   a radial magnetic coupling formed between the impeller radial permanent magnets and the rotor hub radial permanent magnets; and
   pressure forces generated by rotation of the impeller.

3. The blood pump of claim 1, wherein the impeller is configured to be radially supported during rotation by a permanent magnetic bearing formed between the impeller axial permanent magnets and the housing axial permanent magnet.

4. The blood pump of claim 1, wherein the housing axial permanent magnet is a ring magnet.

5. The blood pump of claim 4, wherein the pump housing further comprises an additional ring magnet outside the housing axial permanent magnet.

6. The blood pump of claim 4, wherein the pump housing further comprises an additional ring magnet inside the housing axial permanent magnet.

7. The blood pump of claim 1, wherein the housing axial permanent magnet is one of a series of similarly polarized magnets that form a continuous magnetic field.

8. The blood pump of claim 1, wherein, as the impeller rotates, radial restoring forces generated by the housing axial permanent magnet and the impeller axial permanent magnets are sufficient to overcome radial forces created by an attraction of the impeller radial permanent magnets and the rotor hub radial permanent magnets.

9. The blood pump of claim 1, wherein, radially opposing surfaces of the impeller and the pump housing do not form a radial hydrodynamic bearing.

10. The blood pump of claim 1, wherein, as the impeller rotates, radially opposing surfaces of the impeller and the pump housing are configured to form a radial bearing gap of greater than 0.005".

11. The blood pump of claim 1, wherein, as the impeller rotates, radially opposing surfaces of the impeller and the pump housing are configured to form a radial hydrodynamic bearing.

12. The blood pump of claim 1, wherein the impeller further comprises a hydrodynamic bearing feature on a side of the impeller facing the housing axial permanent magnet.

13. The blood pump of claim 12, wherein the hydrodynamic bearing feature is positioned between the impeller axial permanent magnets and the housing axial permanent magnet.

14. The blood pump of claim 1, wherein, as the impeller rotates, axially opposing surfaces of the impeller and the pump housing are configured to form an axial bearing gap of greater than 0.005".

15. A method of pumping blood, the method comprising:
with a motor, rotating a rotor hub within a first chamber of a pump housing, the rotor hub comprising rotor radial permanent magnets;
with the rotor hub, rotating an impeller within a second chamber of the pump housing, the impeller comprising impeller axial permanent magnets and impeller radial permanent magnets;
radially stabilizing the impeller with a permanent magnetic bearing formed between the impeller axial permanent magnets and a housing axial permanent magnet residing within the pump housing; and
axially stabilizing the impeller with a radial magnetic coupling between the impeller radial permanent magnets and the rotor radial permanent magnets.

16. The method of claim 15, wherein axially stabilizing the impeller comprises maintaining a balance of:
the permanent magnetic bearing;
the radial magnetic coupling; and
pressure forces generated by rotation of the impeller.

17. The method of claim 15, wherein, as the impeller rotates, radial restoring forces generated by the housing axial permanent magnet and the impeller axial permanent magnets are sufficient to overcome radial forces created by an attraction of the impeller radial permanent magnets and the rotor radial permanent magnets.

18. The method of claim 15, wherein, as the impeller rotates, radially opposing surfaces of the impeller and the pump housing do not form a radial hydrodynamic bearing.

19. The method of claim 15, wherein, as the impeller rotates, radially opposing surfaces of the impeller and the pump housing form a radial bearing gap of greater than 0.005".

20. The method of claim 15, wherein, as the impeller rotates, radially opposing surfaces of the impeller and the pump housing form a radial hydrodynamic bearing.

21. The method of claim 15, wherein, as the impeller rotates, axially opposing surfaces of the impeller and the pump housing form an axial bearing gap of greater than 0.005".

\* \* \* \* \*